United States Patent
Zhao

(10) Patent No.: US 9,983,060 B1
(45) Date of Patent: May 29, 2018

(54) CALIBRATION OF A SPECTRAL ANALYSIS MODULE

(71) Applicant: Cymer, LLC, San Diego, CA (US)

(72) Inventor: Zhongquan Zhao, San Diego, CA (US)

(73) Assignee: Cymer, LLC, San Diego, CA (US)

(*) Notice: Subject to any disclaimer, the term of this patent is extended or adjusted under 35 U.S.C. 154(b) by 0 days. days.

(21) Appl. No.: 15/362,033

(22) Filed: Nov. 28, 2016

(51) Int. Cl.
*G01D 18/00* (2006.01)
*G01J 3/50* (2006.01)
*G01N 21/31* (2006.01)
*G01N 21/33* (2006.01)
*G03F 7/20* (2006.01)

(52) U.S. Cl.
CPC .......... *G01J 3/50* (2013.01); *G01N 21/3103* (2013.01); *G01N 21/33* (2013.01); *G03F 7/7055* (2013.01); *G03F 7/70575* (2013.01)

(58) Field of Classification Search
CPC ...... G03F 7/70575; H01S 3/1305; H01S 3/13; H01S 3/137
See application file for complete search history.

(56) References Cited

U.S. PATENT DOCUMENTS

| | | | |
|---|---|---|---|
| 4,585,344 A | 4/1986 | Webster | |
| 4,823,354 A | 4/1989 | Znotins et al. | |
| 5,450,207 A | 9/1995 | Fomenkov | |
| 5,978,391 A * | 11/1999 | Das | G01J 9/00 250/339.13 |
| 6,317,448 B1 * | 11/2001 | Das | G01J 9/00 356/432 |
| 7,006,541 B2 | 2/2006 | Lokai et al. | |
| 9,478,933 B2 | 10/2016 | Suzuki et al. | |
| 2008/0037025 A1 * | 2/2008 | Rafac | G01J 3/02 356/451 |

FOREIGN PATENT DOCUMENTS

WO 9901890 A1 1/1999
WO 9946836 A1 9/1999

OTHER PUBLICATIONS

Reddy, "Laser Optogalvanic Spectroscopy: Experimental Details and Potential Applications in R&D," Defence Science Journal, vol. 44, No. 4, Oct. 1994, pp. 279-293 (15 total pages).

* cited by examiner

*Primary Examiner* — Kenneth J Malkowski
(74) *Attorney, Agent, or Firm* — DiBerardino McGovern IP Group LLC

(57) ABSTRACT

An apparatus includes a material having an optical transition profile with a known energy transition; and a detector configured to detect a characteristic associated with the interaction between the material and the testing light beam. The testing light beam is either a primary light beam produced by an optical source or a calibration light beam. The apparatus also includes a spectral analysis module placed in a path of the primary light beam; and a control system connected to the detector and to the spectral detection system. The control system is configured to determine a reference spectral profile of the primary light beam based on the detected characteristic; compare the reference spectral profile of the primary light beam with a sensed spectral profile of the primary light beam output from the spectral detection system; and based on this comparison, adjust a scale of the spectral detection system.

25 Claims, 10 Drawing Sheets

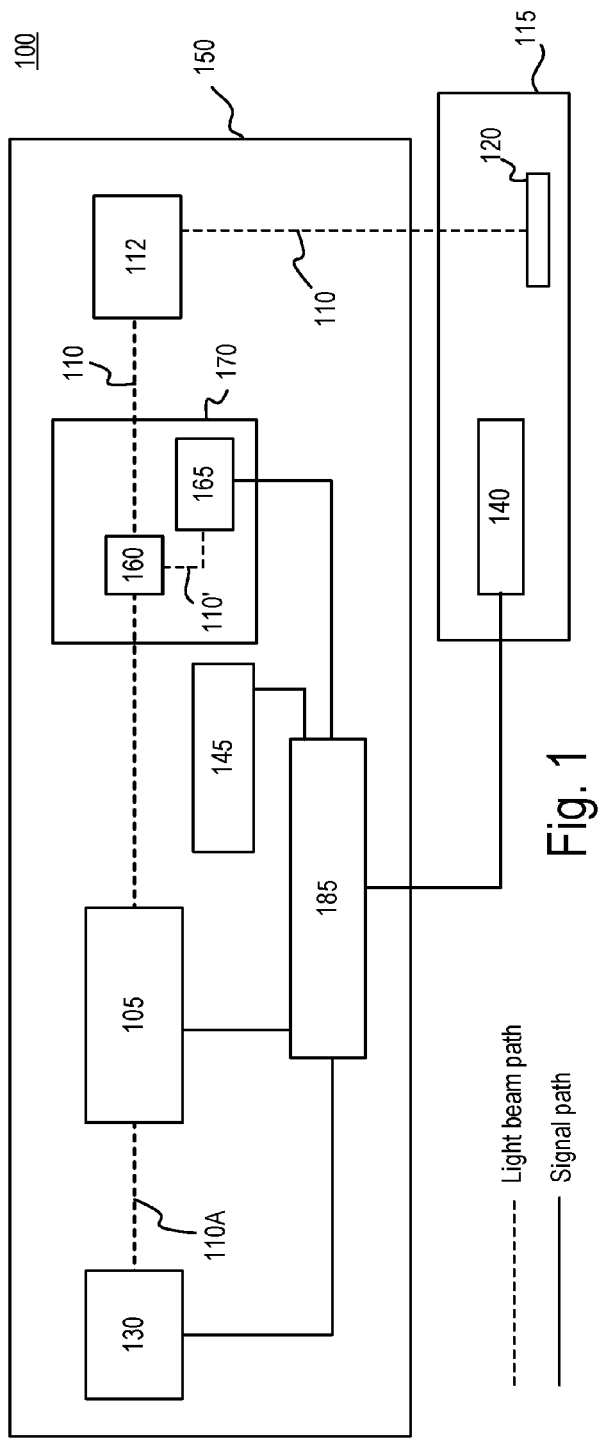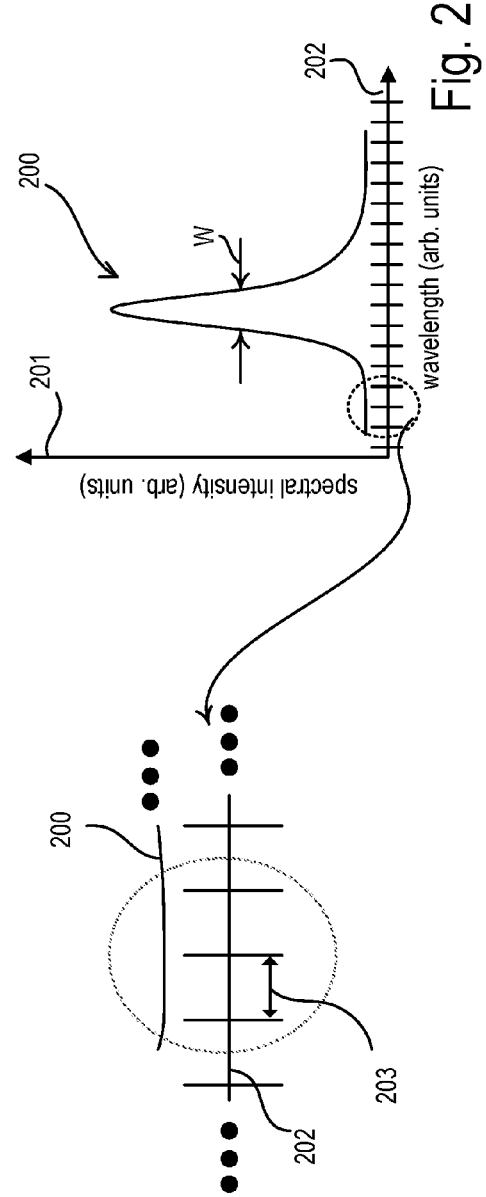

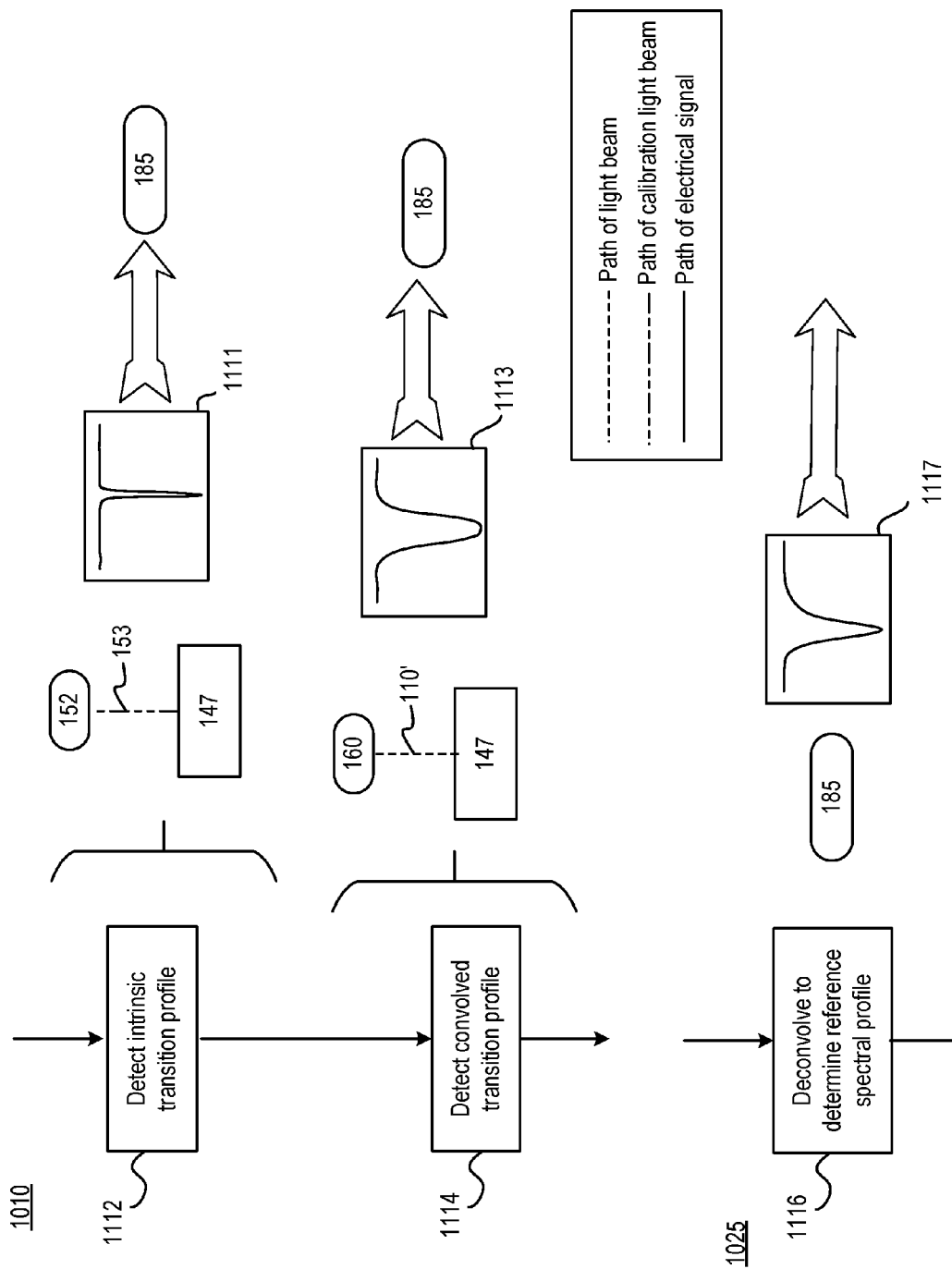

CALIBRATION OF A SPECTRAL ANALYSIS MODULE

TECHNICAL FIELD

The disclosed subject matter relates to an apparatus and method for calibration a spectral analysis module that measures and analyzes a spectral feature, such as, for example, bandwidth or wavelength, of a light beam.

BACKGROUND

In semiconductor lithography (or photolithography), the fabrication of an integrated circuit (IC) includes performing a variety of physical and chemical processes on a semiconductor (for example, silicon) substrate (which is also referred to as a wafer). A photolithography exposure apparatus or scanner is a machine that applies a desired pattern onto a target portion of the substrate. The wafer is irradiated by a light beam that extends along an axial direction, and the wafer is fixed to a stage so that the wafer generally extends along a lateral plane that is substantially orthogonal to the axial direction. The light beam has a wavelength in the deep ultraviolet (DUV) range, for example, from about 10 nanometers (nm) to about 400 nm. The light beam travels along the axial direction (which that is orthogonal to the lateral plane along which the wafer extends).

A spectral analysis module is used to measure spectral features of the light beam, and such measured spectral features are used to control aspects of the light beam, and thereby control a minimum feature size or critical dimension (CD) at the wafer.

SUMMARY

In some general aspects, an apparatus includes: a calibration light source that produces a calibration light beam; a material having an optical transition profile with a known energy transition, wherein the testing light beam is a primary light beam produced by an optical source or the calibration light beam; a detector configured to detect a characteristic associated with the interaction between the material and the testing light beam as the testing light beam is directed through the material while the testing light beam is scanned across the known energy transition; a spectral analysis module placed in a path of the primary light beam, the spectral analysis module including a spectral detection system that senses a spectral profile of the primary light beam; and a control system connected to the detector and to the spectral detection system. The control system is configured to: determine a reference spectral profile of the primary light beam based on the detected characteristic from the detector; compare the reference spectral profile of the primary light beam with the sensed spectral profile of the primary light beam output from the spectral detection system; and based on this comparison, adjust a scale of the spectral detection system.

Implementations can include one or more of the following features. For example, the detector can be configured to detect the characteristic associated with the interaction between the material and the testing light beam by detecting the characteristic associated with the interaction between the material and the primary light beam while the primary light beam is directed through the material and while the wavelength of the primary light beam is scanned across the known energy transition; and the detector can be configured to detect the characteristic associated with the interaction between the material and the testing light beam by detecting of the characteristic associated with the interaction between the material and the calibration light beam while the calibration light beam is directed through the material and while the wavelength of the calibration light beam is scanned across the known energy transition.

The detector can be configured to detect the characteristic associated with the interaction between the material and the testing light beam by detecting an aspect associated with an absorption profile of the testing light beam by the material.

The material can include platinum, and the known energy transition can be an electron transition at 193.4 nanometers. The platinum can be in a vapor or a plasma state.

The spectral analysis module can include an optical frequency separation apparatus that receives the primary light beam, and can be configured to interact with the primary light beam and to output a plurality of spatial components that correspond to the spectral components of the primary light beam, and the spectral detection system receives the plurality of spatial components.

The material can be housed within a cell, and the detector and the cell that houses the material can be configured inside a housing, the housing including an aperture that permits the testing light beam to pass.

The spectral analysis module can include at least one etalon.

The apparatus can also include a spectral feature selection apparatus configured to interact with the primary light beam. The control system can be connected to a controller of the spectral feature selection apparatus.

The control system can be configured to, after adjusting the scale of the spectral detection system: estimate a spectral profile of the primary light beam from the spectral analysis module; estimate a spectral feature of the primary light beam based on the sensed spectral profile; determine if the estimated spectral feature is within an acceptable range of spectral features; and if the estimated spectral feature is not within an acceptable range of spectral features, then send a signal to the controller of the spectral feature selection apparatus to thereby modify one or more properties of the primary light beam to adjust the spectral feature.

The known energy transition can include an electron transition, a vibrational transition, or a rotational transition.

The control system can be configured to adjust the scale of the spectral detection system if it is determined during the comparison that the sensed spectral profile of the primary light beam does not match with the reference spectral profile of the primary light beam.

The characteristic detected by the detector can be an electrical property of a discharge plasma of the material as the material and the testing beam interact. The material can be produced as a discharge plasma from an electrode. The electrode can define a through hole in which the discharge plasma is produced and through which the testing light beam passes.

The material can be housed within a hermetically-sealed cell, and the cell can include an input window and an output window, the input window and the output window being optically transmissive to the wavelength of the testing light beam.

The material can be made up of atoms and/or molecules.

The calibration light source can be a single frequency laser and the calibration light beam can operate in a single resonator mode.

The characteristic detected by the detector can be an intensity of the testing beam that has interacted with the material.

The material and the detector can be housed within an enclosure that is within either the housing of the spectral analysis module or the housing of the spectral detection system.

The control system can be configured to compare the reference spectral profile of the primary light beam with the sensed spectral profile of the primary light beam by comparing two or more values of the reference spectral profile of the primary light beam with two or more values of the sensed spectral profile of the primary light beam.

The control system can be configured to adjust the scale of the spectral detection system by adjusting a relative distance between two or more values of wavelength of the primary light beam.

The material and the testing light beam can be configured to be positioned either in a first arrangement in which the testing light beam is directed through the material or a second arrangement in which the testing light beam is not directed through the material.

In other general aspects, a method includes: detecting an intrinsic transition profile of a known energy transition of a calibration material by detecting a characteristic associated with the interaction between the material and a calibration light beam while the calibration light beam is directed through the calibration material and while the wavelength of the calibration light beam is scanned across the known energy transition; and detecting a convolved transition profile in which the intrinsic transition profile is altered by a spectral shape of a primary light beam, wherein detecting the convolved transition profile comprises detecting a characteristic associated with the interaction between the material and the primary light beam while the primary light beam is directed through the calibration material and while the wavelength of the primary light beam is scanned across the known energy transition. The method also includes deconvolving the intrinsic transition profile from the spectral shape of the primary light beam within the detected convolved transition profile to determine a reference spectral profile of the primary light beam; sensing a spectral profile of the primary light beam, the spectral profile including an optical energy of the primary light beam distributed over different values of a spectral feature; comparing the reference spectral profile of the primary light beam with the sensed spectral profile of the primary light beam; and adjusting a scale of the different values of the spectral feature at which the spectral profile of the primary light beam is estimated based on the comparison.

Implementations can include one or more of the following features. For example, the characteristic associated with the interaction between the material and the calibration light beam can be detected by detecting an aspect of the calibration material that changes as an amount of absorption of the calibration light beam by the calibration material changes. The method can also include producing a discharge plasma of the calibration material, and detecting the aspect of the calibration material that changes can include detecting an electrical property of a discharge plasma of the calibration material.

The characteristic associated with the interaction between the material and the primary light beam can be detected by detecting an aspect of the calibration material that changes as an amount of absorption of the primary light beam by the calibration material changes. The method can include producing a discharge plasma of the calibration material, and detecting the aspect of the calibration material that changes can include detecting an electrical property of a discharge plasma of the calibration material.

The method can also include storing the intrinsic transition profile.

The spectral profile of the primary light beam can be sensed by sensing the optical energy of the primary light beam distributed over different values of the wavelength of the primary light beam. The reference spectral profile of the primary light beam can be compared with the sensed spectral profile of the primary light beam by comparing two or more values of the reference spectral profile with two or more values of the sensed spectral profile. Two or more values of the reference spectral profile can be compared with two or more values of the sensed spectral profile by comparing a relative distance between the two or more values of the reference spectral profile of the primary light beam with a relative distance between two or more values of the sensed spectral profile of the primary light beam. The scale of the different values of the spectral feature at which the spectral profile of the primary light beam is sensed can be adjusted by adjusting the scale if the relative distance of the reference spectral profile of the primary light beam is different from the relative distance of the sensed spectral profile of the primary light beam.

The method can also include, after adjusting the scale: estimating a spectral profile of the primary light beam; estimating a spectral feature of the primary light beam based on the estimated spectral profile; determining if the estimated spectral feature is within an acceptable range of spectral features; and if the estimated spectral feature is not within an acceptable range of spectral features, then modifying one or more properties of the primary light beam to adjust the spectral feature.

The known energy transition can include an electron transition, a vibrational transition, or a rotational transition.

The scale of the different values of the spectral feature at which the spectral profile of the primary light beam is sensed can be adjusted by adjusting the scale if it is determined during the comparison that the sensed spectral profile of the primary light beam does not match with the reference spectral profile of the primary light beam.

DESCRIPTION OF DRAWINGS

FIG. 1 is a block diagram of an exemplary photolithography system that includes a calibration apparatus that is used to calibrate a metrology system that measures one or more spectral features of a light beam produced by the photolithography system;

FIG. 2 is a graph of an exemplary optical spectrum of a pulsed light beam produced by the photolithography system of FIG. 1;

FIG. 11 are flow charts of procedures for detecting a characteristic associated with an interaction between a material having a known energy transition and a testing light beam and for determining a reference spectral profile of the light beam of the photolithography system of FIG. 1 using the calibration apparatus;

DESCRIPTION

Figure 3:
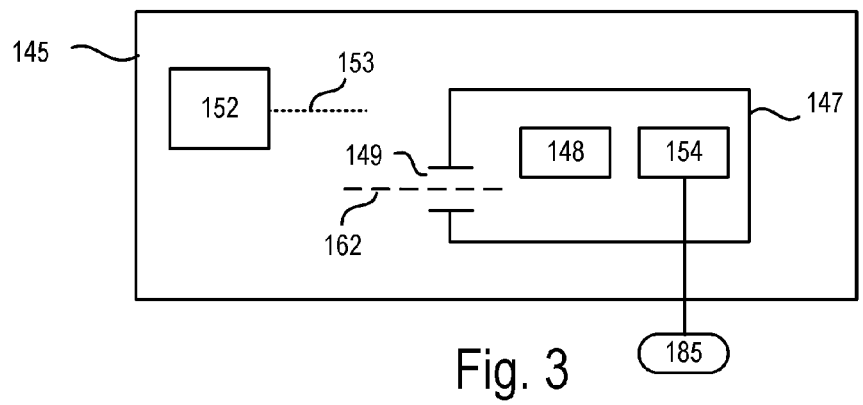
FIG. 3 is a block diagram of an exemplary calibration apparatus for use in the photolithography system of FIG. 1.

Referring to FIG. 1, a photolithography system 100 includes an illumination system 150 that produces a pulsed light beam 110 having a wavelength that is nominally at a center wavelength and is directed to a photolithography exposure apparatus or scanner 115 by way of a beam preparation system 112 that can include beam directing and beam modification optics. The pulsed light beam 110 is produced by an optical source 105 and is directed to a wafer 120 in the exposure apparatus 115 to thereby pattern microelectronic features on the wafer 120. The light beam 110 has a wavelength in the deep ultraviolet (DUV) range, for example, about 248 nanometers (nm) or about 193 nm. The size of the microelectronic features patterned on the wafer 120 depends on the wavelength of the light beam 110, with a lower wavelength resulting in a smaller minimum size. When the wavelength of the light beam 110 is 248 nm or 193 nm, the minimum size of the microelectronic features can be, for example, 50 nm or less. Moreover, the bandwidth of the light beam 110 can impact the critical dimension (CD) of these features.

Various disturbances (such as, for example, temperature gradients, pressure gradients, optical distortions) act on the optical source 105 and the light beam 110 to modify the spectral properties or features (such as the bandwidth and the wavelength) of the light beam 110. For example, chromatic aberration caused by optical components that interact with the light beam 110 can cause an increase in the bandwidth of the light beam 110. Thus, the lithography system 100 includes other components, such as, for example, a spectral feature selection system 130, at least one metrology (or measurement) system 170, and a control system 185, that are used in combination to determine the impact of the disturbances on the light beam 110 and to correct for the effect of such disturbances on the light beam 110.

Because of the disturbances, the actual spectral feature (such as the bandwidth or the wavelength) of the light beam 110 at the wafer 120 may not correspond to or match with the desired spectral feature. Thus, the metrology system 170 measures or senses the actual spectral feature (such as a bandwidth or the wavelength) of light beam 110 during operation of the optical source 105 by estimating a value of a metric from a measured optical spectrum 200 (shown in FIG. 2). An operator or an automated system (for example, the control system 185) can use the measured or sensed bandwidth of the light beam 110 to adjust the properties of the optical source 105 (for example, by sending a signal to the spectral feature selection system 130) and to thereby adjust the optical spectrum (and the spectral features) of the light beam 110. The optical spectrum 200 can be referred to as the spectral shape or intensity spectrum of the light beam 110. The control system 185 receives the output of the metrology system 170 and analyzes the sensed spectral profile and estimates one or more spectral features of the light beam 110 based on this analysis.

During operation, the accuracy of the metrology system 170 can deteriorate because of various unwanted effects. In one unwanted effect, the metrology system 170 may have been calibrated in an inaccurate manner using an external spectrometer. For example, an external spectrometer can have a calibration accuracy of about 50 femtometers (fm) and this accuracy is limited by the inaccuracy of the measurement within the external spectrometer. In another effect, over time, optical components (such as an etalon or a lens) within the metrology system 170 can degrade over time due to interaction between these optical components and the light beam 110. For example, the finesse of the etalon within the metrology system 170 can degrade upon repeated interaction between the etalon and the light beam 110. Moreover, the resolving power of the etalon is proportional to the etalon's finesse and inversely proportional to the free spectral range of the etalon. Thus, the resolving power of the etalon within the metrology system 170 deteriorates if the finesse of the etalon is degraded by exposure to the light beam 110 (assuming that the free spectral range does not appreciably change). These effects deteriorate the accuracy of the measurements made by the metrology system 170, and thus make it difficult to accurately determine the spectral feature (such as the bandwidth) of the light beam 110, and accordingly, it becomes difficult to control the spectral features of the light beam 110 at the wafer 120.

In order to improve the accuracy of measurements of a spectral feature or features such as the bandwidth within the metrology system 170, the photolithography system 100 includes a calibration apparatus 145 that provides an absolute reference for the spectral feature of the light beam 110 that is to be measured. For example, the calibration apparatus 145 can provide an absolute reference for the bandwidth of the light beam 110 and this can be referred to as an absolute bandwidth reference (ABR). The calibration apparatus 145 uses a spectral profile of a known energy transition to provide the absolute bandwidth reference, as discussed below. Moreover, the control system 185 can compare the absolute bandwidth reference (ABR) with the spectral profile or the bandwidth of the light beam 110' that is sensed by the metrology system 170 to determine whether the metrology system 170 needs to be calibrated or recalibrated (if previously calibrated). Calibration of the metrology system 170 involves adjusting the scale of the measurement component or components of the metrology system 170 so as to improve the accuracy of the measurements of the spectral feature (such as the bandwidth) provided by the metrology system 170.

Specifically, the metrology system 170 outputs the optical spectrum 200 of the light beam 110', and from the optical spectrum 200 (as shown in FIG. 2), the control system 185 estimates the actual, instantaneous bandwidth of the light beam 110'. The optical spectrum 200 contains information about how the optical energy or power of the light beam 110' is distributed over different wavelengths (or frequencies) 202. A scale 203 of the optical spectrum 200 is a measure of a relative distance between the wavelengths 202. The optical spectrum 200 of the light beam 110 is depicted in the form of a diagram in which the spectral intensity 201 is plotted as a function of the wavelength or optical frequency 202. Spectral properties or features of the light beam 110 include any aspect or representation of this optical spectrum 200. For example, bandwidth is a spectral feature. The bandwidth of the light beam 110 is a measure of the width W of this optical spectrum 200, and this width W can be given in terms of wavelength or frequency of the laser light. Any suitable mathematical construction (for example, metric) related to the details of the optical spectrum 200 can be used to estimate a value that characterizes the bandwidth of the light beam. For example, the full width of the optical spectrum 200 at a fraction (X) of the maximum peak intensity of the spectral shape (referred to as FWXM) can be used to characterize the light beam bandwidth. In an example, the fraction X is 50%. As another example, the width of the optical spectrum 200 that contains a fraction (Y) of the integrated spectral intensity (referred to as EY) can be used to characterize the light beam bandwidth. In an example, the fraction Y is 95%.

The accuracy of the measurement of the bandwidth W of the light beam 110 depends, at least in part, on whether the wavelength scale 203 is accurate. The calibration apparatus 145 provides the spectral profile of the known energy transition (which can be referred to as a reference spectral profile) to provide the absolute bandwidth reference ABR to the control system 185, and the control system 185 uses this reference spectral profile (that provides an absolute bandwidth reference or ABR) to determine whether the scale 203 of the sensed spectral profile (optical spectrum 200) provides accurate values for the bandwidth measurement W. For example, the ABR (which is the width measured from the reference spectral profile) is compared with the sensed bandwidth W of the light beam 110', and if sensed bandwidth W does not match the ABR, then the control system 185 determines how much the sensed bandwidth W deviates from the ABR to determine how to adjust the scale 203 of the metrology system 170. For example, if the control system 185 determines that the scale 203 is not accurate (because the sensed bandwidth W deviates too much from the ABR), then the control system 185 can send a signal to the metrology system 170 that adjusts the scale 203 (for example, widens or narrow the distance between the wavelength values 202). In general, because the calibration apparatus 145 is used to provide an absolute bandwidth reference, and the bandwidth is determined based on two or more aspects of the optical spectrum (such as the value of the width W discussed above), the comparison between the reference spectral profile (which provides the absolute bandwidth reference) and the sensed spectral profile (of the optical spectrum 200) involves comparing at least two data points from the reference spectral profile with at least two data points from the sensed spectral profile. Moreover, the adjustment to the metrology system 170 therefore involves adjusting the scale 203, which is the relative difference between two wavelength values 202.

Referring to FIG. 3, the calibration apparatus 145 includes a calibration tool 147 and a calibration light source 152 that produces a calibration light beam 153. The calibration tool 147 includes an aperture 149 and at least one detector 154 that communicates with the control system 185. Moreover, the calibration tool 147 houses a material 148 having an optical transition profile with the known energy transition. A testing light beam 162 (which can be either the calibration light beam 153 or the light beam 110') interacts with the material 148 to produce an transition (for example, absorption) profile of the energy transition of the material 148, and this transition profile is detected by the detector 154.

The transition profile shows the relationship between a characteristic associated with the interaction between the testing light beam 162 and the material 148 and the wavelength of the testing light beam 162. Thus, in order to detect the transition profile, the wavelength of the testing light beam 162 should be measured as it is scanned across the energy transition. There are two scenarios for measuring the wavelength of the testing light beam 162. One scenario uses the wavelength metrology built into the light source that produces the testing light beam 162, for example, wavelength metrology within the calibration light source 152 or the optical source 105. The problem with this approach is that the wavelength measuring accuracy or resolution for the calibration light source 152 and the optical source 105 could be different from each other, and this difference would introduce inaccuracy in the de-convoluted spectrum of the light beam 110'. Another scenario is to use the same wavelength metrology for both the calibration light beam 153 and the light beam 110'. For example, the line analysis module within the light beam 110' can be used to measure the wavelength of both the calibration light beam 153 and the light beam 110' when detecting the transition profile.

The calibration light source 152 can be a single frequency laser and the calibration light beam 153 is quasi-monochromatic radiation having a very small bandwidth and low phase noise. For example, the calibration light source 152 can be a light source that operates in a single resonator mode to provide the quasi-monochromatic radiation. The excited mode can be a Gaussian mode, so that the calibration light beam 153 is diffraction limited. The calibration light source 152 is selected so that the wavelength of the calibration light beam 153 can be scanned across the known energy transition of the material 148, and this wavelength should be within the wavelength range of the light beam 110. Thus, if the material 148 has a known energy transition in the DUV wavelength, then the calibration light source 152 produces a calibration light beam 153 that has a wavelength that can be scanned across a range of DUV wavelengths. In some implementations, the calibration light source 152 is a single frequency all-solid-state laser system in which the gain medium is pumped by a diode laser to produce a calibration light beam 153 operating in the lowest order transverse electromagnetic resonator mode, the $TEM_{00}$ mode. The spectral linewidth (or bandwidth) of the calibration light beam 153 can be a fraction of the size of the bandwidth of the light beam 110. For example, if the bandwidth of the light beam 110 is on the order of 300 fm, then the spectral linewidth of the calibration light beam 153 can be a factor of ten smaller than this value, for example, on the order of 10-30 fm.

The material 148 can be made of atoms or molecules. The material 148 can be any material that has a known energy transition that coincides with the wavelength range of the light beam 110. Thus, as mentioned above, if the light beam 110 has a wavelength in the DUV range, then the material 148 is selected and the known energy transition is selected to be in that same DUV range. In some implementations, the material 148 is platinum that has a known transition at 193.4 nm.

The interaction between the testing light beam 162 (which can be the light beam 110' or the calibration light beam 153) and the material 148 causes a change in one or more characteristics of the light beam 110 and/or the material 148 if the wavelength of the light beam 110 overlaps the known energy transition wavelength. This change in the characteristic is detected by the detector 154 and from this changing characteristic, the spectral profile of the testing light beam 162 can be estimated.

The known energy transition that is monitored within the material 148 can be an electron transition, a vibrational transition, or a rotational transition. These energy transitions are due to the fact that the particles (for example, atoms or molecules) within the material 148 take on certain discrete values of energy, and these discrete values are called energy levels. The term "energy levels" is used for the energy levels of electrons in atoms, ions, or molecules, which are bound by the electric field of the nucleus, but can also refer to energy levels of nuclei or vibrational or rotational energy levels in molecules.

For example, the energy transition can be an electron transition within an atomic or a molecular material. The electron transition is a change of an electron from one quantum state to another within the material 148. It appears discontinuous as the electron "jumps" from one energy level to another in a few nanoseconds or less. Such an electron transition causes the emission or absorption of electromagnetic radiation in the form of photons.

As another example, the energy transition that is monitored may be a more complex transition if the material 148 is molecular, because a molecular material is more chemically complex than an atomic material. In this case, the energy transition can involve changes in either or both vibrational and rotational states of the material 148. When such transitions emit or absorb photons (electromagnetic radiation), the frequency is proportional to the difference in energy levels and can be detected by certain kinds of spectroscopy.

The material 148 can be inside a vapor cell or enclosure. In some implementations, as discussed below, the material 148 is produced as a discharge plasma and is a part of a laser galvatron, which is an opto-galvanic sensor that takes advantage of the resonance phenomenon between the discharge plasma of the material 148 and the testing light beam (which can be the light beam 110' or the calibration light beam 153). This is discussed in greater detail below with reference to FIG. 4.

The aperture 149 provides a path for receiving a testing light beam (such as the light beam 110' or the calibration light beam 153). The control system 185 analyzes the absorption profiles of the energy transition due to the interaction between the testing light beam and the material 148 to determine whether the metrology system 170 needs to be calibrated, for example, by adjusting the scale at which the metrology system 170 measures the spectral feature or features of the light beam 110'. The calibration apparatus 145 may include components other than those shown in FIG. 3.

Figure 4:
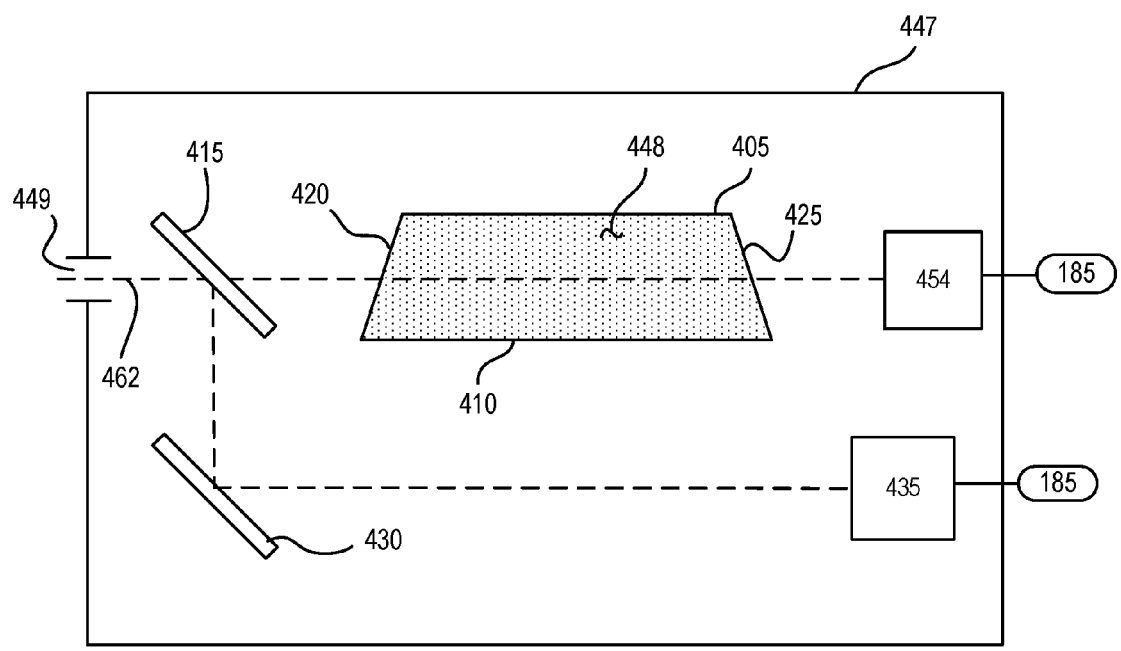
FIG. 4 is a block diagram of an exemplary calibration tool for use in the calibration apparatus of FIG. 1 or 3.

Referring to FIG. 4, an exemplary calibration tool 447 is shown. In this calibration tool 447, the material 448 is housed in a cell 405. The cell 405 is defined by a wall 410 that is made of a rigid and chemically inert substance that retains the material 448. The substance of the wall 410 should not interact with the material 448 or the testing light beam 462 (which can be the calibration light beam 153 or the light beam 110'). Moreover, the cell 405 includes at least an input window 420 and an output window 425 through which the testing light beam 462 can pass. The cell 405 is sealed from the external environment in order to contain the material 448.

The calibration tool 447 also includes the detector 454. The detector 454 is set up to detect the characteristic associated with the interaction between the material 448 and the testing light beam 462 as the testing light beam 462 is directed through the material 448 and while the wavelength of the testing light beam 462 is scanned across the known energy transition.

The calibration tool 447 can also include a beam splitter 415 that redirects a portion of the testing light beam 462 toward a mirror 430 and a detector 435 to monitor the power of the testing light beam 462 to normalize the signal sensed by the detector 454.

The calibration tool 447 can operate as a galvatron in which the material 448 is a gas or plasma discharge produced from an electrode that is made of the material and placed within the cell 405.

Opto-galvanic spectroscopy can be used in some implementations. In opto-galvanic spectroscopy, the current passing through the gas discharge (which is the material 448) is monitored by the detector 454 as the testing light beam 462 is tuned through the frequencies of allowed transitions for excited atoms or molecules in the gas discharge. When the testing light beam 462 resonantly excites an atom or molecule from a low-lying state to a state of higher excitation, for example, that atom or molecule is excited to a less bound state, thereby increasing the probability that the atom or molecule will be ionized by discharge collisions and contribute to an increase in the discharge current. This small change in discharge current can be detected with great sensitivity by the detector 454. In contrast to other spectroscopic methods that could be used to detect the characteristic associated with the interaction between the testing light beam 462 and the material 448, opto-galvanic spectroscopy does not require an optical detector (such as a photomultiplier tube or photodiode detector) to obtain atomic transition spectra, because the gas discharge itself serves as a resonant photodetector.

In other implementations, optical spectroscopy is used. In these implementations, the detector 454 is an optical detector such as a photodiode detector or a photomultiplier tube that measures an intensity of the testing light beam 462 that has passed through the material 448.

In some implementations, the calibration tool 447 is configured as a field-service tool, which is standalone component that includes a housing that holds the cell 405 and the detector 454 as well as an aperture 449 that permits the testing light beam 462 to pass. In other implementations, the calibration tool 447 is integrated into the metrology system 170. In some implementations, the calibration tool 447 is configured to automatically calibrate the metrology system 170 on a periodic basis.

Figure 5:
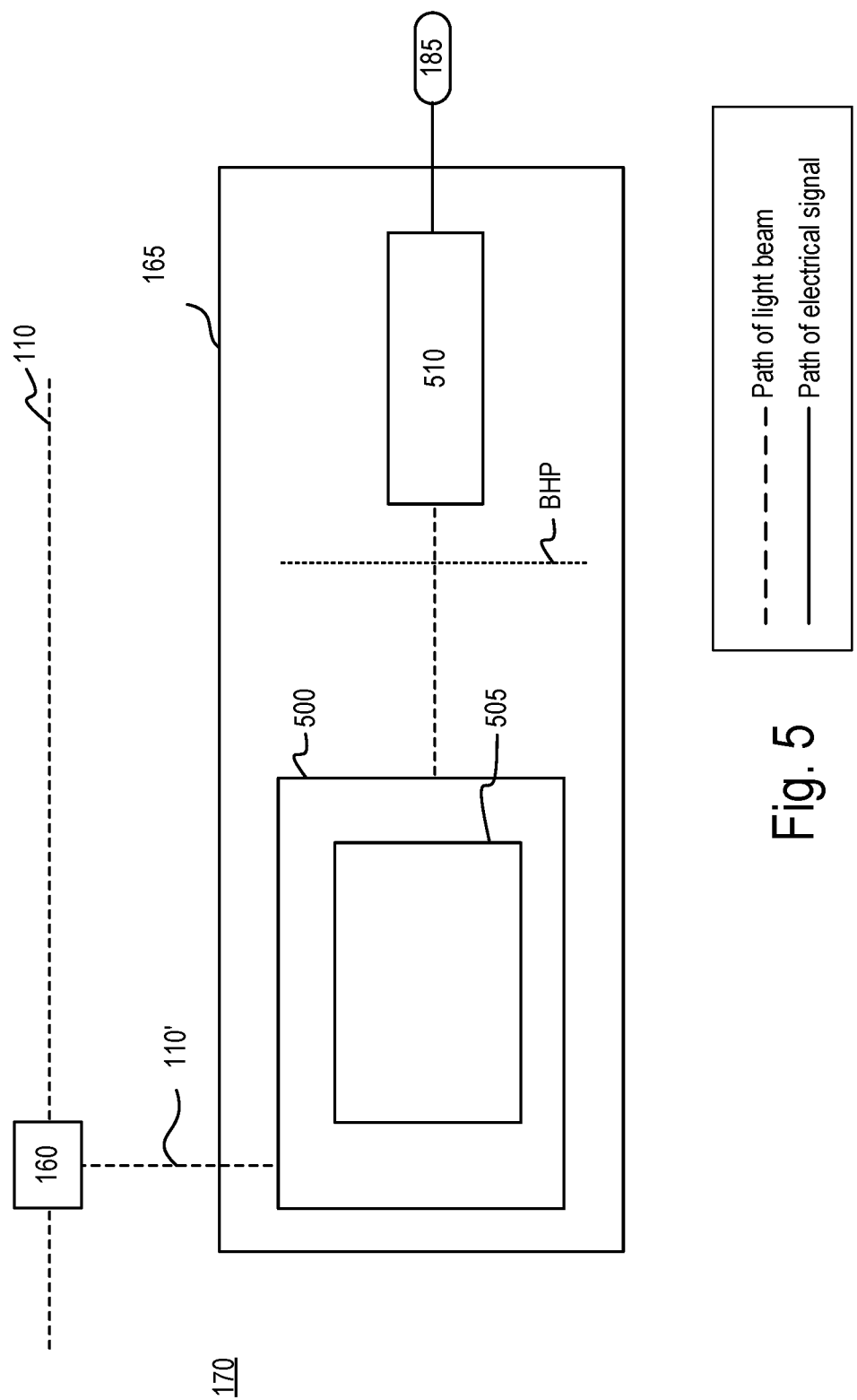
FIG. 5 is a block diagram of an exemplary metrology system for use in the photolithography system of FIG. 1.

Referring to FIG. 5, the metrology system 170 includes the beam separator 160 and the diagnostic apparatus 165. The diagnostic apparatus 165 receives the light beam 110' that is separated from the light beam 110 by the beam separator 160. The beam separator 160 is placed in a path between the optical source 105 and the photolithography exposure apparatus 115. The beam separator 160 directs the light beam 110' (which is a first portion or percentage of the light beam 110) into the diagnostic apparatus 165 and directs a second portion or percentage of the light beam 110 toward the exposure apparatus 115. In some implementations, the majority of the light beam 110 is directed in the second portion toward the exposure apparatus 115. For example, the beam separator 160 directs a fraction (for example, 1-2%) of the light beam 110 into the diagnostic apparatus 165 and thus the light beam 110' has about 1-2% of the power of the light beam 110. The beam separator 160 can be, for example, a beam splitter.

The diagnostic apparatus 165 includes a spectral detection system 510 that measures the spectral feature or features (such as the bandwidth and/or the wavelength) of the light beam 110 based on information about the optical spectrum 200 of the light beam 110'. As discussed herein, the spectral detection system 510 include a spectrometer (such as an etalon spectrometer) that interacts with the light beam 110' and outputs spatial components that correspond to the spectral components of the light beam 110', and a sensor that estimates the spectral feature or features based on the outputted spatial components.

In order to uniformly sample the spectral content of the light beam 110' at the sensor, to evenly distribute the intensity of the light beam 110' at the sensor, and to provide a more accurate measurement of the spectral feature from the sensor, the diagnostic apparatus 165 includes a beam homogenizer 505 that is a part of a beam preparation system 500. The beam homogenizer 505 reduces speckle noise and improves beam homogenization of the light beam 110' impinging upon the sensor of the spectral detection system 510. The spectral content of the light beam 110' is mixed and the intensity profile of the light beam 110' is smoothed at the beam homogenization plane (BHP) prior to the light beam 110' entering the etalon spectrometer of the spectral detection system 510.

The beam homogenizer 505 can include other elements or components for modifying aspects of the light beam 110'. For example, the beam homogenizer 505 can also include a pulse stretcher system, a diffuser system, and a spatial adjustment system. The pulse stretcher system is a pulse stretcher that optically acts on the light beam 110' to increase a duration of the pulses in the light beam 110" without introducing significant losses so that the peak power of the light beam 110' is reduced without reducing its average power. The pulse stretcher system can further reduce the optical speckle noise that can be found at the homogenized beam plane. The pulse stretcher system is an optical and passive configuration of optical elements that split the amplitude of the pulse of the light beam 110' into split portions, introduce optical delays among these split portions, and then recombine these temporally-delayed portions of the pulse to provide a temporally stretched pulse of the light beam 110' at the output. In this way, different temporal portions of the pulse that are not coherent are combined, and the speckle noise of the light beam 110' is reduced and therefore the spatial uniformity of the light beam 110' is improved.

The diffuser system includes one or more optical elements that are configured to evenly diffuse the light beam 110'. The diffuser system causes the light beam 110' to spread evenly across a plane transverse to the direction along which the light beam 110' travels, thus minimizing or removing high intensity bright spots. The diffuser system can alter the angular divergence of the light beam 110'. The diffuser system smoothes out or otherwise mitigates diffraction spikes that can sometimes be produced within the beam homogenizer 505. The diffuser system can be a microlens array or a diffractive optic (which can be transmissive or reflective).

The spatial adjustment system works to refract the light beam 110' to spread out the spacing between diffraction spikes that can be created within the beam homogenizer 505. In this way, the spacing between the diffraction spikes can be increased by the spatial adjustment system so that the spacing is larger than a region of interest of the sensor within the spectral detection system 510. The spatial adjustment system can be a lens that is positioned so that its focal plane overlaps a beam homogenization plane produced by the beam homogenizer 505.

Figure 6:
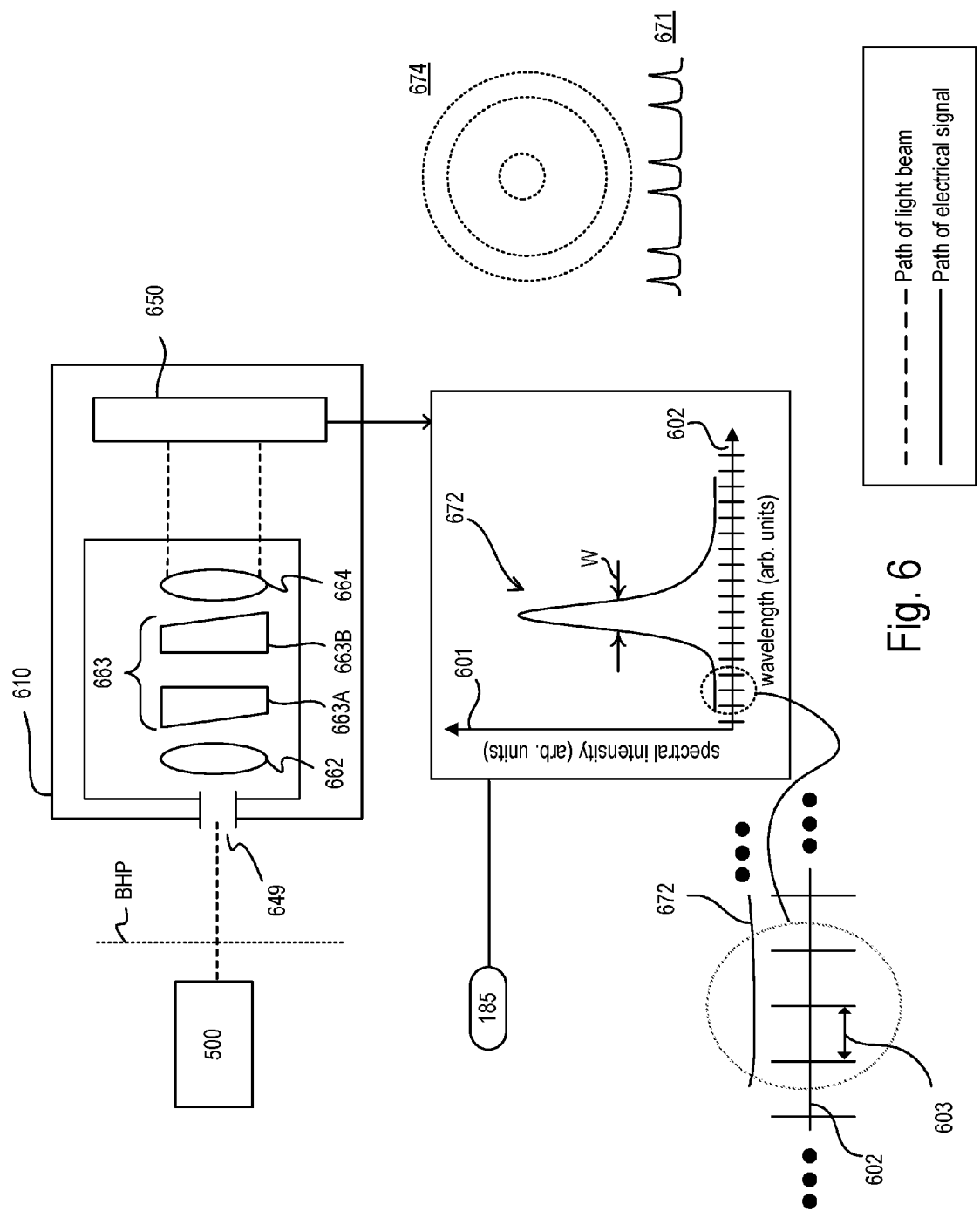
FIG. 6 is a block diagram of an exemplary spectral detection system within the metrology system of FIG. 1.

Referring also to FIG. 6, a spinning diffuser can be placed at the beam homogenization plane BHP, which is the plane at which the light beam 110' has been homogenized. The spinning diffuser is a diffuser that is rotated about the direction of the path of the light beam 110'. The diffuser diffuses the light beam 110' to a cone to fill an aperture 649 of an exemplary spectral detection system 610. The spinning diffuser also reduces any spikes in the intensity within the light beam 110' that can result from interference of the copies of the spatial modes sampled within the beam homogenizer 505 of the beam preparation system 500. Moreover, the aperture 649 is placed at a focal plane FP (662) of an input lens 662 within the spectral detection system 610. By locating the aperture 649 of the spectral detection system 610 at the focal plane FP (662) of the input lens 662, each point from the focal plane FP (662) acts as a point source and accordingly, the input lens 662 acts to collimate the light beam 110' before entering an optical frequency separation apparatus (which can be an etalon 663). An output lens 664 is positioned at the exit of the etalon 663 so that its focal plane FP (664) of the output lens 664 overlaps the active area of the sensor 650.

In some implementations, the etalon 663 includes a pair of partially reflective glass or optical flats 663A, 663B, which can be spaced a short distance (for example, millimeters to centimeters) apart, with the reflective surfaces facing each other. In other implementations, the etalon 663 includes a single plate with two parallel reflecting surfaces. The flats 663A, 663B can be made in a wedge shape to prevent the rear surfaces from producing interference fringes; the rear surfaces often also have an anti-reflective coating. As the light beam 110' passes through the paired flats 663A, 663B, it is multiply reflected, and produces a plurality of transmitted rays, which are collected by the output lens 664 and brought to the active region of the sensor 650. The spectral detection system 510 also can include an optical relay, as needed, between the output lens 664 and the sensor 650 to ensure that the sensor 650 is at the focal plane of the output lens 664.

The etalon 663 interacts with the light beam 110' and outputs a plurality of spatial components 674 that correspond to the spectral components of the light beam 110'. The spectral components of the light beam 110' are in the optical spectrum 672 of the light beam 110'; therefore, they correspond to how the values of the optical energy or power (the spectral intensity 601) of the light beam 110' are distributed over the different wavelengths 602. The spatial components 674 correspond to these intensities mapped into a two-dimensional space. Thus, the etalon 663 transforms the spectral information (such as the wavelength) of the light beam 110' into spatial information that can be sensed or detected by the sensor 650. The transformation maps the spectral information (such as the wavelength) to different positions in space so that the spectral information that can be observed by the sensor 650.

The etalon 663 produces as the spatial components 674 an interference pattern that takes the appearance of a set of concentric rings. The interference pattern takes the appearance of a more uniform intensity distribution if the intensity distribution of the light beam 110' on the aperture 649 is more uniform. In particular, the sharpness of the rings depends on the reflectivity of the flats 663A, 663B of the etalon 663. Thus, if the reflectivity of the flats 663A, 663B is high (such that the etalon has a high quality (Q) factor), when the beam 110' is a monochromatic light beam, the etalon 663 produces a set of narrow bright rings against a dark background. The transmission of the etalon 663 as a function of wavelength is shown in the resulting fringe pattern 671, which produces the optical spectrum 672 that is directed to the control system 185.

While the complete interference pattern is shown, it is not needed to perform the calculations or estimates; it is alternatively possible to generate only fringes within a region that is slightly larger than an active area of the sensor 650.

The sensor 650 receives and senses the output spatial components 674. The sensor 650 can be defined by a plane that indicates generally the active area of its sensing region. The plane of the sensing region can be perpendicular to the direction of propagation of the spatial components 674.

The sensor 650 can be a detector that receives and senses the output spatial components 674. For example, one type of suitable detector that can be used to measure along one dimension is a linear photodiode array. The linear photodiode array is consists of multiple elements of the same size, formed in a linear arrangement at an equal spacing in one package. The photodiode array is sensitive to the wavelength of the light beam 110', and if the light beam 110' has a wavelength in the deep ultraviolet range, then the photodiode array is sensitive to light having a wavelength in the deep ultraviolet range. As another example, the sensor 650 can be a two dimensional sensor such as a two-dimensional charged coupled device (CCD) or a two-dimensional complementary metal oxide semiconductor (CMOS) sensor. The sensor 650 should be able to read out data at a fast enough rate, for example, at about 6 kHz.

The control system 185 is connected to the output of the sensor 650 as well as the optical source 105 and the spectral feature selection system 130 that is optically coupled to the light beam 110. The control system 185 measures a property of the spatial components 674, and analyzes these measured properties to calculate an estimate of the spectral feature of the light beam 110. The control system 185 can perform the measurement, analysis, and calculation for each pulse of the light beam 110 or for a set of pulses of the light beam 110.

The property P that is measured can be a scalar quantity (which is fully described by a magnitude or numerical value) alone or a vector quantity (which is fully described by both a magnitude and a direction). An example of a scalar property P is a metric such as the width W of the optical spectrum 672. In this example, it is possible that the entire shape of the optical spectrum 672 is not known but the metric is known and this is used to estimate the shape of the optical spectrum 672. An example of a vector property P is the entire waveform that describes the optical spectrum 672. In this example, one can calculate any metric from the entire spectrum and the by having the entire spectrum, one can make a more accurate calculation. The sensed spatial components can be measured for a range of one or more pulses of the pulsed light beam 110'.

The control system 185 can measure as the property P the width W of the optical spectrum 672. The width W of the optical spectrum 672 can provide an estimate of the bandwidth (the spectral feature) of the light beam 110'. In some implementations, the width W of the optical spectrum 672 is determined using a metric such as the FWXM (full width of the spectrum 672 at a fraction X of the maximum peak intensity). In other implementations, the width W of the optical spectrum 672 is determined using a metric such as EY (the width of the spectrum that contains a fraction Y of the integrated spectral intensity). Other metrics are suitable for measuring the property of the optical spectrum 672.

As discussed above, calibration of the metrology system 170 involves adjusting a scale 603 of the output from the sensor 650. For example, if the control system 185 determines that the scale 603 is not accurate (because the sensed bandwidth W deviates too much from the ABR output from the calibration apparatus 145), then the control system 185 can send a signal to the metrology system 170 that adjusts the scale 603 (for example, widens or narrow the distance between the wavelength values 602).

Before this calibration method is discussed, the other components of the photolithography system 100 are described.

Figure 7:
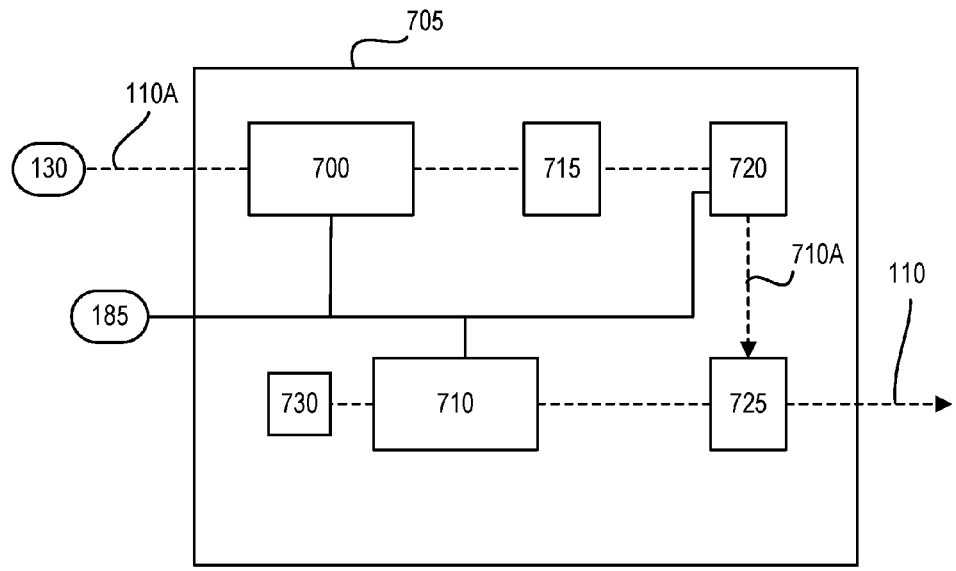
FIG. 7 is a block diagram of an exemplary optical source that produces the light beam of the photolithography system of FIG. 1.

Referring to FIG. 7, in some implementations, the optical source 105 is an exemplary optical source 705. The optical source 705 is a pulsed laser source that produces a pulsed laser beam as the light beam 110. The optical source 705 is a two-stage laser system that includes a master oscillator (MO) 700 that provides the seed light beam 710A to a power amplifier (PA) 710. The master oscillator 700 typically includes a gain medium in which amplification occurs and an optical feedback mechanism such as an optical resonator. The power amplifier 710 typically includes a gain medium in which amplification occurs when seeded with the seed laser beam from the master oscillator 700. If the power amplifier 710 can be a power ring amplifier (PRA), which is designed as a regenerative ring resonator. In this case, enough optical feedback can be provided from the ring design. The spectral feature selection apparatus 130 receives the light beam 110A from the master oscillator 700 to enable fine tuning of spectral parameters such as the center wavelength and the bandwidth of the light beam 110A at relatively low output pulse energies. The power amplifier 710 receives the light beam 710A from the master oscillator 700 and amplifies this output to attain the necessary power for output to use in photolithography.

The master oscillator 700 includes a discharge chamber having two elongated electrodes, a laser gas that serves as the gain medium, and a fan circulating the gas between the electrodes. A laser resonator is formed between the spectral feature selection apparatus 130 on one side of the discharge chamber, and an output coupler 715 on a second side of the discharge chamber to output the seed light beam 710A to the power amplifier 710.

The optical source 705 can also include a line center analysis module (LAM) 720 that receives an output from the output coupler 715, and one or more beam modification optical systems 725 that modify the size and/or shape of the beam as needed. The line center analysis module 720 is an example of one type of measurement system that can be used to measure the wavelength (for example, the center wavelength) of the seed light beam.

The power amplifier 710 includes a power amplifier discharge chamber, and if it is a regenerative ring amplifier, the power amplifier also includes a beam reflector or beam turning device 730 that reflects the light beam back into the discharge chamber to form a circulating path. The power amplifier discharge chamber includes a pair of elongated electrodes, a laser gas that serves as the gain medium, and a fan for circulating the gas between the electrodes. The seed light beam 710A is amplified by repeatedly passing through the power amplifier 710. The beam modification optical system 725 provides a way (for example, a partially-reflecting mirror) to in-couple the seed light beam 710A and to out-couple a portion of the amplified radiation from the power amplifier to form the output light beam 110.

The laser gas used in the discharge chambers of the master oscillator 700 and the power amplifier 710 can be any suitable gas for producing a laser beam around the required wavelengths and bandwidth. For example, the laser gas can be argon fluoride (ArF), which emits light at a wavelength of about 193 nm, or krypton fluoride (KrF), which emits light at a wavelength of about 248 nm.

The line center analysis module 720 monitors the wavelength of the output (the light beam 710A) of the master oscillator 700. The line center analysis module 720 can be placed at other locations within the optical source 705, or it can be placed at the output of the optical source 705.

The repetition rate of the pulses produced by the power amplifier 710 is determined by the repetition rate at which the master oscillator 700 is controlled by the control system 185, under the instructions from a controller 140 in the exposure apparatus 115. The repetition rate of the pulses output from the power amplifier 710 is the repetition rate seen by the exposure apparatus 115.

As discussed above, it is possible to control the bandwidth both coarsely and finely using only optical elements. On the other hand, it is possible to control the bandwidth in a fine and narrow range, and rapidly, by controlling a differential timing between the activation of the electrodes within the MO 700 and the PRA 710 while controlling the bandwidth in a coarse and wide range by adjusting the angle of a prism within the spectral feature selection system 130.

Figure 8:
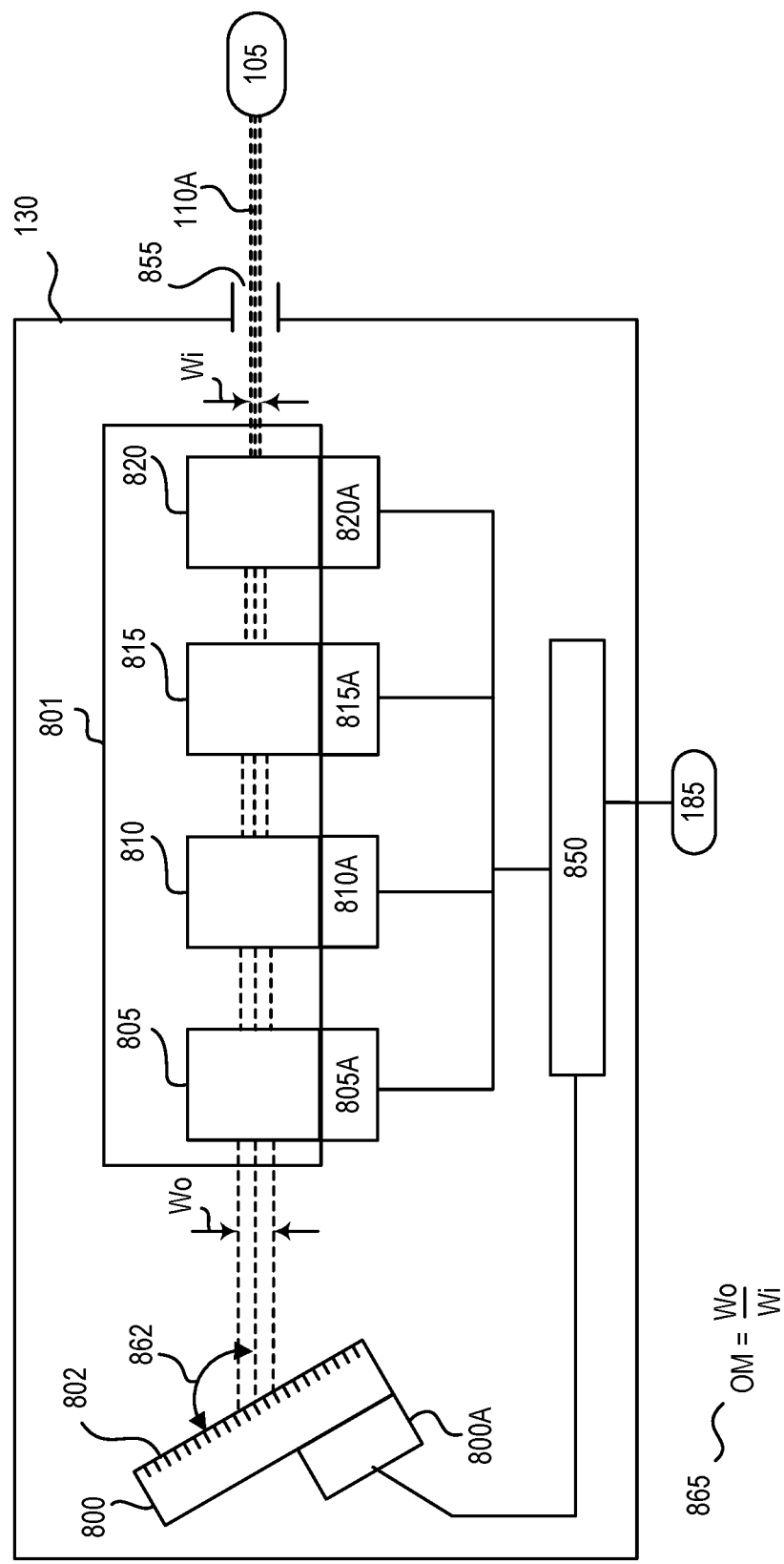
FIG. 8 is a block diagram of an exemplary spectral feature selection system that adjusts a spectral feature of the light beam of the photolithography system of FIG. 1.

Referring to FIG. 8, in some implementations, the spectral feature selection apparatus 130 includes a set of optical features or components 800, 805, 810, 815, 820 arranged to optically interact with the pulsed light beam 110A and a control module 850 that includes electronics in the form of any combination of firmware and software. The optical components 800, 805, 810, 815, 820 can be configured to provide a coarse spectral feature adjustment system; and, if the adjustment of such components is rapid enough, it can be configured to provide a fine spectral feature adjustment system. Although not shown in FIG. 8, it is possible for the spectral feature selection apparatus 130 to include other optical features or other non-optical features for providing fine spectral feature control.

The control module 850 is connected to one or more actuation systems 800A, 805A, 810A, 815A, 820A physically coupled to respective optical components 800, 805, 810, 815, 820. The optical components of the apparatus 130 include a dispersive optical element 800, which can be a grating, and a beam expander 801 made of a set of refractive optical elements 805, 810, 815, 820, which can be prisms. The grating 800 can be a reflective grating that is designed to disperse and reflect the light beam 110A; accordingly, the grating 800 is made of a material that is suitable for interacting with a pulsed light beam 110A having a wavelength in the DUV range. Each of the prisms 805, 810, 815, 820 is a transmissive prism that acts to disperse and redirect the light beam 110A as it passes through the body of the prism. Each of the prisms can be made of a material (such as, for example, calcium fluoride) that permits the transmission of the wavelength of the light beam 110A. Although four refractive optical elements 805, 810, 815, 820 are shown, it is possible for fewer than four or more than four to be used in the beam expander 801.

The pulsed light beam 110A enters the apparatus 130 through an aperture 855, and then travels through the prism 820, the prism 810, and the prism 1005, in that order, prior to impinging upon a diffractive surface 802 of the grating 800. With each passing of the beam 110A through a consecutive prism 820, 815, 810, 805, the light beam 110A is optically magnified and redirected (refracted at an angle) toward the next optical component. The light beam 110A is diffracted and reflected from the grating 800 back through the prism 805, the prism 810, the prism 815, and the prism 820, in that order, prior to passing through the aperture 855 as the light beam 110A exits the apparatus 130. With each passing through the consecutive prisms 805, 810, 815, 820 from the grating 800, the light beam 110A is optically compressed as it travels toward the aperture 855.

The rotation of a prism (which can be any one of prisms 805, 810, 815, 820) of the beam expander 801 changes an angle of incidence at which the light beam 110A impinges upon the entrance surface of that rotated prism. Moreover, two local optical qualities, namely, an optical magnification and a beam refraction angle, of the light beam 110A through that rotated prism are functions of the angle of incidence of the light beam 110A impinging upon the entrance surface of that rotated prism. The optical magnification of the light beam 110A through the prism is the ratio of a transverse wide of the light beam 110A exiting that prism to a transverse width of the light beam 110A entering that prism.

A change in the local optical magnification of the light beam 110A at one or more of the prisms within the beam expander 801 causes an overall change in the optical magnification OM 865 of the light beam 110A through the beam expander 801. The optical magnification OM 865 of the light beam 110A through the beam expander 801 is the ratio of the transverse width Wo of the light beam 110A exiting the beam expander 801 to a transverse width Wi of the light beam 110A entering the beam expander 801. Additionally, a change in the local beam refraction angle through one or more of the prisms within the beam expander 801 causes an overall change in an angle of incidence of 862 of the light beam 110A at the surface 802 of the grating 800. The wavelength of the light beam 110A can be adjusted by changing the angle of incidence 862 at which the light beam 110A impinges upon the diffractive surface 802 of the grating 800. The bandwidth of the light beam 110A can be adjusted by changing the optical magnification 865 of the light beam 110.

The apparatus 130 is designed to adjust the wavelength of the light beam 110A that is produced within the resonator or resonators of the optical source 105 by adjusting an angle 862 of incidence of at which the light beam 110A impinges upon the diffractive surface 802 of the grating 800. Specifically, this can be done by rotating one or more of the prisms 805, 810, 815, 820 and the grating 800 to thereby adjust the angle of incidence 862 of the light beam 110A.

Moreover, the bandwidth of the light beam 110A that is produced by the optical source 105 is adjusted by adjusting the optical magnification OM 865 of the light beam 110A. Thus, the bandwidth of the light beam 110A can be adjusted by rotating one or more of the prisms 805, 810, 815, 820, which causes the optical magnification 865 of the light beam 110A to change. Because the rotation of a particular prism causes a change in both the local beam refraction angle and the local optical magnification at that prism, the control of wavelength and bandwidth are coupled in this design.

Additionally, the bandwidth of the light beam 110A is relatively sensitive to the rotation of the prism 820 and relatively insensitive to rotation of the prism 805. This is because any change in the local optical magnification of the light beam 110A due to the rotation of the prism 820 is multiplied by the product of the change in the optical magnification in the other prisms 815, 810, and 805 because those prisms are between the rotated prism 820 and the grating 800, and the light beam 110A must travel through these other prisms 815, 810, 805 after passing through the prism 820. On the other hand, the wavelength of the light beam 110A is relatively sensitive to the rotation of the prism 805 and relatively insensitive to the rotation of the prism 820.

For example, in order to change the bandwidth without changing the wavelength, the optical magnification 865 should be changed without changing the angle of incidence 862, and this can be achieved by rotating the prism 820 by a large amount and rotating the prism 805 by a small amount.

The control module 850 is connected to one or more actuation systems 800A, 805A, 810A, 815A, 820A that are physically coupled to respective optical components 800, 805, 810, 815, 820. Although an actuation system is shown for each of the optical components it is possible that some of the optical components in the apparatus 130 are either kept stationary or are not physically coupled to an actuation system. For example, in some implementations, the grating 800 can be kept stationary and the prism 815 can be kept stationary and not physically coupled to an actuation system.

Each of the actuation systems 800A, 805A, 810A, 815A, 820A includes one or more actuators that are connected to its respective optical components. The adjustment of the optical components causes the adjustment in the particular spectral features (the wavelength and/or bandwidth) of the light beam 110A. The control module 850 receives a control signal from the control system 185, the control signal including specific commands to operate or control one or more of the actuation systems. The actuation systems can be selected and designed to work cooperatively.

Each of the actuators of the actuation systems 800A, 805A, 810A, 815A, 820A is a mechanical device for moving or controlling the respective optical component. The actuators receive energy from the module 850, and convert that energy into some kind of motion imparted to the respective optical component. For example, the actuation systems can be any one of force devices and rotation stages for rotating one or more of prisms of a beam expander. The actuation systems can include, for example, motors such as stepper motors, valves, pressure-controlled devices, piezoelectric devices, linear motors, hydraulic actuators, voice coils, etc.

The grating 800 can be a high blaze angle Echelle grating, and the light beam 110A incident on the grating 800 at any angle of incidence 862 that satisfies a grating equation will be reflected (diffracted). The grating equation provides the relationship between the spectral order of the grating 800, the diffracted wavelength (the wavelength of the diffracted beam), the angle of incidence 862 of the light beam 110A onto the grating 800, the angle of exit of the light beam 110A diffracted off the grating 800, the vertical divergence of the light beam 110A incident onto the grating 800, and the groove spacing of the diffractive surface of the grating 800. Moreover, if the grating 800 is used such that the angle of incidence 862 of the light beam 110A onto the grating 800 is equal to the angle of exit of the light beam 110A from the grating 800, then the grating 800 and the beam expander (the prisms 805, 810, 815, 820) are arranged in a Littrow configuration and the wavelength of the light beam 110A reflected from the grating 800 is the Littrow wavelength. It can be assumed that the vertical divergence of the light beam 110A incident onto the grating 800 is near zero. To reflect the nominal wavelength, the grating 800 is aligned, with respect to the light beam 110A incident onto the grating 800, so that the nominal wavelength is reflected back through the beam expander (the prisms 805, 810, 815, 820) to be amplified in the optical source 105. The Littrow wavelength can then be tuned over the entire gain bandwidth of the resonators within optical source 105 by varying the angle of incidence 862 of the light beam 110A onto the grating 800.

Each of the prisms 805, 810, 815, 820 is wide enough along the transverse direction of the light beam 110A so that the light beam 110A is contained within the surface at which it passes. Each prism optically magnifies the light beam 110A on the path toward the grating 800 from the aperture 855, and therefore each prism is successively larger in size from the prism 820 to the prism 805. Thus, the prism 805 is larger than the prism 810, which is larger than the prism 815, and the prism 820 is the smallest prism.

As discussed above, the bandwidth of the light beam 110A is relatively sensitive to the rotation of the prism 820 and relatively insensitive to rotation of the prism 805. This is because any change in the local optical magnification of the light beam 110A due to the rotation of the prism 820 is multiplied by the product of the change in the optical magnification in the other prisms 815, 810, and 805 because those prisms are between the rotated prism 820 and the grating 800, and the light beam 110A must travel through these other prisms 815, 810, 805 after passing through the prism 820. On the other hand, the wavelength of the light beam 110A is relatively sensitive to the rotation of the prism 805 and relatively insensitive to the rotation of the prism 820. Thus, the wavelength can be coarsely changed by rotating the prism 805, and the prism 820 can be rotated (in a coarse manner). The angle of incidence 862 of the light beam 110A is changed due to the rotation of the prism 805 and the rotation of the prism 820 offset the change in magnification caused by the rotation of the prism 805. The prism 820 can be used for coarse, large range, and slow bandwidth control. By contrast, the bandwidth can be controlled in a fine and narrow range and even more rapidly by controlling the prism 810.

Figure 9:
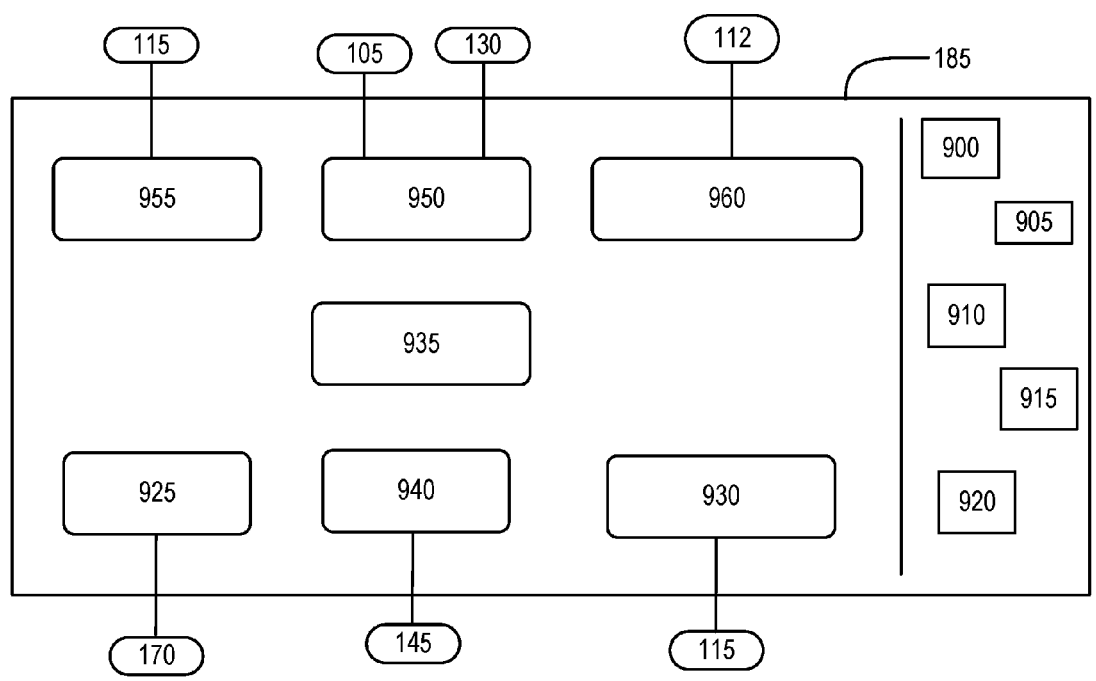
FIG. 9 is a block diagram of an exemplary control system of the photolithography system of FIG. 1.

Referring to FIG. 9, details about the control system 185 are provided that relate to the aspects of the system and method described herein. The control system 185 can include other features not shown in FIG. 9. In general, the control system 185 includes one or more of digital electronic circuitry, computer hardware, firmware, and software.

The control system 185 includes memory 900, which can be read-only memory and/or random access memory. Storage devices suitable for tangibly embodying computer program instructions and data include all forms of non-volatile memory, including, by way of example, semiconductor memory devices, such as EPROM, EEPROM, and flash memory devices; magnetic disks such as internal hard disks and removable disks; magneto-optical disks; and CD-ROM disks. The control system 185 can also include one or more input devices 905 (such as a keyboard, touch screen, microphone, mouse, hand-held input device, etc.) and one or more output devices 910 (such as a speaker or a monitor).

The control system 185 includes one or more programmable processors 915, and one or more computer program products 920 tangibly embodied in a machine-readable storage device for execution by a programmable processor (such as the processors 915). The one or more programmable processors 915 can each execute a program of instructions to perform desired functions by operating on input data and generating appropriate output. Generally, the processor 915 receives instructions and data from memory 900. Any of the foregoing may be supplemented by, or incorporated in, specially designed ASICs (application-specific integrated circuits).

The control system 185 includes, among other components, a spectral feature analysis module 925, a lithography analysis module 930, a decision module 935, a calibration module 940, a light source actuation module 950, a lithography actuation module 955, and a beam preparation actuation module 960. Each of these modules can be a set of computer program products executed by one or more processors such as the processors 915. Moreover, any of the modules 925, 930, 935, 940, 950, 955, 960 can access data stored within the memory 900.

The spectral feature analysis module 925 receives the output from the metrology system 170. The calibration module 940 receives the output of the detector 154 (or detectors 454, 435) from the calibration apparatus 145 (or 445). The lithography analysis module 930 receives information from the lithography controller 140 of the exposure apparatus 115. The decision module 935 receives the outputs from the analyses modules (such as the modules 925, 930, and 940) and determines which actuation module or modules need to be activated based on the outputs from the analyses modules. The light source actuation module 950 is connected to one or more of the optical source 105 and the spectral feature selection apparatus 130. The lithography actuation module 955 is connected to the exposure apparatus 115, and specifically to the lithography controller 140. The beam preparation actuation module 960 is connected to one or more components of the beam preparation system 112. Connections between modules within the control system 185 and between modules within the control system 185 and other components of the photolithography system 100 can be wired or wireless.

While only a few modules are shown in FIG. 9, it is possible for the control system 185 to include other modules. Additionally, although the control system 185 is represented as a box in which all of the components appear to be co-located, it is possible for the control system 185 to be made up of components that are physically remote from each other. For example, the light source actuation module 950 can be physically co-located with the optical source 105 or the spectral feature selection apparatus 130.

In general, the control system 185 receives at least some information about the light beam 110 from the metrology system 170, and the spectral feature analysis module 925 performs an analysis on the information to determine how to adjust one or more spectral features (for example, the bandwidth) of the light beam 110 supplied to the exposure apparatus 115. Based on this determination, the control system 185 sends signals to the spectral feature selection apparatus 130 and/or the optical source 105 to control operation of the optical source 105 via the control module 850. In general, the spectral feature analysis module 925 performs the analysis needed to estimate one or more spectral features (for example, the wavelength and/or the bandwidth) of the light beam 110. The output of the spectral feature analysis module 925 is an estimated value of the spectral feature that is sent to the decision module 935.

The spectral feature analysis module 925 includes a comparison block connected to receive the estimated spectral feature and also connected to receive a spectral feature target value. In general, the comparison block outputs a spectral feature error value that represents a difference between the spectral feature target value and the estimated value. The decision module 935 receives the spectral feature error value and determines how best to effect a correction to the system 100 in order to adjust the spectral feature. Thus, the decision module 935 sends a signal to the light source actuation module 950, which determines how to adjust the spectral feature selection apparatus 130 (or the optical source 105) based on the spectral feature error value. The output of the light source actuation module 950 includes a set of actuator commands that are sent to the spectral feature selection apparatus 130. For example, the light source actuation module 950 sends the commands to the control module 850, which is connected to the actuation systems within the exemplary apparatus 130 shown in FIG. 3.

Additionally, the lithography analysis module 930 can receive instructions from the lithography controller 140 of the exposure apparatus 115 for example, to change one or more spectral features of the pulsed light beam 110 or to change a pulse repetition rate of the light beam 110. The lithography analysis module 930 performs an analysis on these instructions to determine how to adjust the spectral features and sends the results of the analysis to the decision module 935. The control system 185 causes the optical source 105 to operate at a given repetition rate. More specifically, the exposure apparatus 115 sends a trigger signal to the optical source 105 (by way of the control system (through the lithography analysis module 930) for every pulse (that is, on a pulse-to-pulse basis) and the time interval between those trigger signals can be arbitrary, but when the exposure apparatus 115 sends trigger signals at regular intervals then the rate of those signals is a repetition rate. The repetition rate can be a rate requested by the exposure apparatus 115.

The calibration module 940 receives the output from the detector 154, and thus, receives the spectral profiles of the known energy transition. Specifically, as discussed below, these spectral profiles can be used by the calibration module 940 to determine the absolute spectral feature reference (which can be the absolute bandwidth reference, or ABR), and the calibration module 940 uses the ABR to determine whether the scale 203 of the sensed spectral profile (the optical spectrum 200) output from the metrology system 170 and analyzed by the spectral feature analysis module 925 matches with the ABR. Thus, the calibration module 940 compares the ABR with the sensed bandwidth W of the light beam 110' from the spectral feature analysis module 925, and, if sensed bandwidth W does not match the ABR, then the calibration module 940 determines how much the sensed bandwidth W deviates from the ABR to determine how to adjust the scale 203 of the metrology system 170. For example, if the calibration module 940 determines that the scale 203 is not accurate (because the sensed bandwidth W deviates too much from the ABR), then this determination can be directed to the decision module 935. The decision module 935 can output a signal indicating that the scale of the metrology system 170 needs to be adjusted. For example, the signal can be automatically sent to the spectral feature analysis module 925, which is connected to metrology system 170, to thereby adjust the scale automatically. Or, the signal can be output to an operator who can adjust the scale manually.

Figure 10:
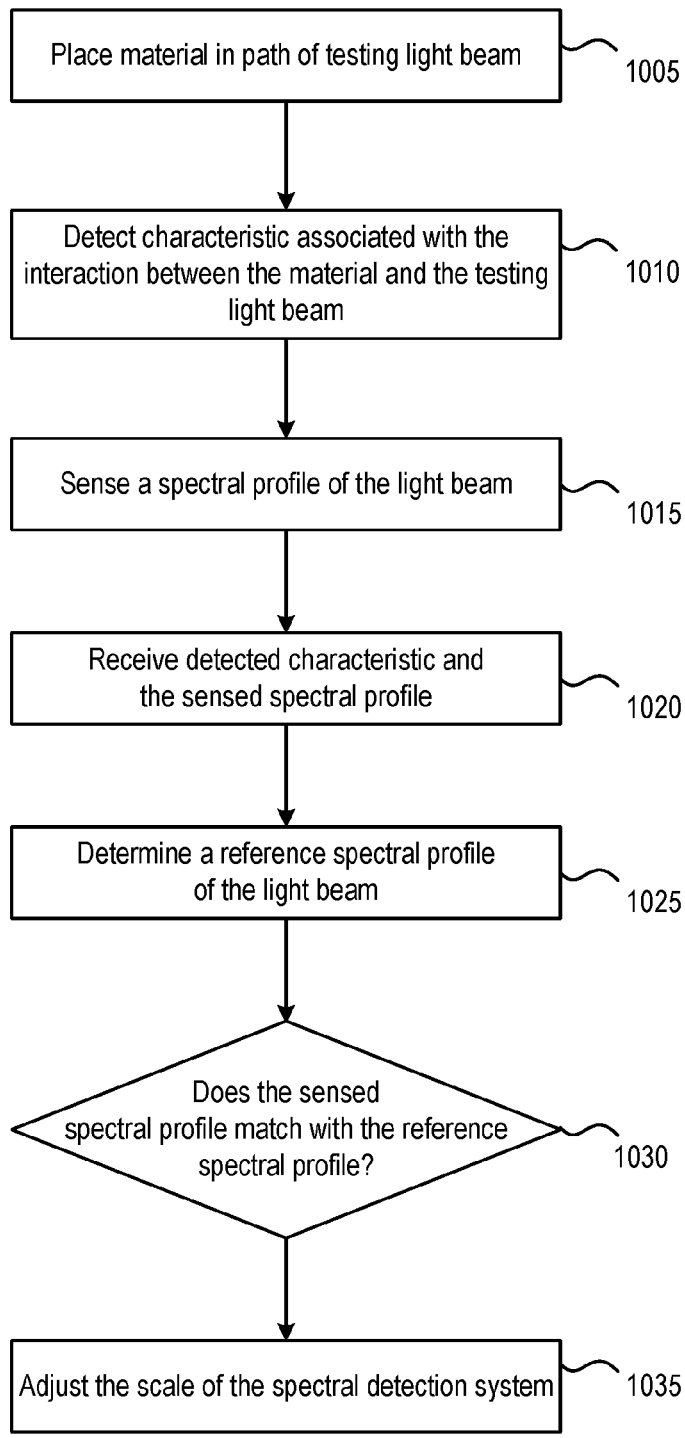
FIG. 10 is a flow chart of a procedure performed by the photolithography system for calibrating the metrology system using the calibration apparatus.

Referring to FIG. 10, a procedure 1000 is performed by the photolithography system 100 to determine whether to calibrate and then, if needed, to perform the calibration of the metrology system 170.

Initially, the material 148 is placed into a path of a testing light beam (1005). The testing light beam can be the calibration light beam 153 or the light beam 110'. A characteristic or characteristics associated with the interaction between the material 148 and the testing light beam is detected, and this is detected while the testing light beam is directed through the material and while the testing light beam is scanned across the known energy transition (1010). For example, the detector 154 of the calibration apparatus 145 detects this characteristic. The spectral profile of the light beam 110' is sensed (for example, by the spectral detection system 510 of the metrology system 170) (1015). The control system 185 receives the characteristic detected by the detector 154 and the spectral profile sensed by the metrology system 170 (1020). A reference spectral profile of the light beam 110' is determined based on the detected characteristic from the detector 154 (1025). For example, the calibration module 940 of the control system 185 can make this determination. The sensed spectral profile of the light beam 110' output from the spectral detection system 510 is compared with the reference spectral profile of the light beam 110' output from the calibration apparatus 145 (1030). The calibration module 940 of the control system 185 can perform this comparison. For example, the calibration module 940 can compare two or more data values or points of the reference spectral profile of the light beam 110' with two or more data values or points of the sensed spectral profile of the light beam 110' to determine if these data values match. In one example, the calibration module 940 compares a width W of the reference spectral profile of the light beam 110' with a width W of the sensed spectral profile of the light beam 110' to determine whether the width of the sensed spectral profile of the light beam 110' matches that of the reference spectral profile.

A width of the sensed spectral profile of the light beam 110' can match the width of the reference spectral profile if the width of the sensed spectral profile of the light beam 110' is within a range of values centered on the reference spectral profile. This range of values can depend on how the widths are measured, that is, the mathematical construct or metric that is used to estimate the widths and the accuracy of the measurement of the width of the sensed spectral profile. The width of the sensed spectral profile of the light beam 110' can be estimated using the E95 metric, and it can be estimated based on an average of a set of widths that are estimated for a plurality of pulses (for example, a burst of pulses) of the light beam 110'. For example, the width can be estimated by taking the average of the widths of each of 300 pulses of the light beam 110. The accuracy of estimating the width of the sensed spectral profile of the light beam 110' using the E95 metric and averaging over a burst of pulses can be about 5 fm. In this example, a difference between the width of the sensed spectral profile of the light beam 110' and the width of the reference spectral profile that is less than this accuracy (that is, 5 fm) can be considered as a match.

The scale of the spectral detection system 510 is adjusted if the comparison indicates that the sensed spectral profile of the light beam 110' does not match the reference spectral profile of the light beam 110' (1035). With reference to FIG. 2, the scale 203 can be adjusted by adjusting a relative distance between two points (two values of the wavelength 202). For example, the control system 185 can send a signal to the metrology system 170 to adjust the scale. As another example, it is possible for the control system 185 to instead output a signal that indicates how the scale of the spectral detection system 510 should be adjusted and, based on that signal, an operator of the photolithography system 100 can make the adjustment to the spectral detection system 510 manually. The adjustment to the spectral detection system 510 can be done in any suitable manner. For example, the adjustment can be to simply add an offset to the spectral profile of the light beam 110' that is sensed by the spectral detection system 510 whenever there is a mismatch between the sensed spectral profile of the light beam 110' and the reference spectral profile of the light beam 110 (1035). As another example, the adjustment can be to adjust the instrumentation function of the metrology system 170 until the width of the sensed spectral profile of the light beam 110' matches the width of the reference spectral profile.

Referring also to FIG. 11, a procedure 1010 is performed by the photolithography system 100 to detect the characteristic or characteristics associated with the interaction between the material 148 and the testing light beam while the testing light beam is directed through the material and while the testing light beam is scanned across the known energy transition.

An intrinsic transition profile 1111 of a known energy transition of the calibration material 148 is detected (1112). The intrinsic transition profile 1111 can be detected by detecting a characteristic associated with the interaction between the material 148 and the calibration light beam 153 while the calibration light beam 153 is directed through the calibration material 148 and while the wavelength of the calibration light beam 153 is scanned across the known energy transition. The intrinsic transition profile 1111 is similar to an instrument function or transfer function of the material 148. Specifically, the calibration light beam 153 is directed through the material 148. And, the characteristic associated with this interaction is detected. The calibration light beam 153 is scanned across the wavelengths that are known to be associated with the known energy transition so that the entire energy transition is recorded in the intrinsic transition profile 1111.

Moreover, the calibration light beam 153 can be scanned across the wavelengths using any suitable scanning technique. The calibration light source 152 is a single frequency laser and is typically tuned in wavelength by one of several methods. The first exemplary method is to change the temperature of the materials used to generate the calibration light beam 153. For example, the temperature of the gain medium (which can be crystals) used to produce single frequency DUV light at 193.4 nm can be adjusted. The second exemplary method mean is to adjust the current of a seed diode laser within the calibration light source 152 if the calibration light source 152 includes a seed diode laser. The third exemplary method is to adjust the incidence angle to the grating if the cavity of the seed light source within the calibration light source 152 includes a grating.

As discussed above, the calibration tool 447 can be operated as a galvatron, and in this case, the material 448 is a gas or plasma discharge produced from an electrode that is made of the material and placed within the cell 405. As discussed above, the detector 454 can be an optical detector such as a photodiode detector or a photomultiplier tube that measures an intensity of the calibration light beam 153 that has passed through the material 448. In other implementations that use opto-galvanic spectroscopy, the current passing through the gas discharge (which is the material 448) is monitored by the detector 454 as the calibration light beam 153 is tuned through the frequencies of allowed transitions for excited atoms or molecules in the gas discharge. Thus, when the calibration light beam 153 resonantly excites an atom or molecule from a low-lying state to a state of higher excitation, the discharge current is changed, and this small change in discharge current can be detected with great sensitivity by the detector 454. This discharge current reproduces the atomic transition spectra, because the gas discharge itself serves as a resonant photodetector.

Because the calibration light beam 153 has a much narrower bandwidth than the bandwidth of the light beam 110', the intrinsic transition profile 1111 provides an instrument response function associated with the material 148.

Next, a convolved transition profile 1113 in which the intrinsic transition profile 1111 is altered by a spectral shape of the light beam 110' is detected (1114). The convolved transition profile 1113 includes the intrinsic transition profile 1111, which has been broadened by the spectral bandwidth of the light beam 110'. The convolved transition profile 1113 can be detected by detecting a characteristic associated with the interaction between the material 148 and the light beam 110' while the light beam 110' is directed through the material 148 and while the wavelength of the light beam 110' is scanned across the known energy transition. Specifically, the light beam 110' is directed through the material 148. And, the characteristic associated with this interaction is detected. The light beam 110' is scanned across the wavelengths that are known to be associated with the known energy transition so that the entire energy transition is recorded in the convolved transition profile 1113. Moreover, the light beam 110' can be scanned across the wavelengths using any suitable scanning technique. For example, with reference to FIG. 8, the wavelength of the light beam 110 and therefore the light beam 110' can be tuned by angularly rotating the wavelength control prism 805, 810, 815, or 820, which changes the angle of incidence 862 of the light beam 110A on the grating 800.

As discussed above, the calibration tool 447 is operated as a galvatron, then the material 448 is a gas or plasma discharge produced from an electrode that is made of the material and placed within the cell 405. As discussed above, the detector 454 can be an optical detector such as a photodiode detector or a photomultiplier tube that measures an intensity of the light beam 110' that has passed through the material 448. In other implementations that use optogalvanic spectroscopy, the current passing through the gas discharge (which is the material 448) is monitored by the detector 454 as the light beam 110' is tuned through the frequencies of allowed transitions for excited atoms or molecules in the gas discharge. Thus, when the light beam 110' resonantly excites an atom or molecule from a low-lying state to a state of higher excitation, the discharge current is changed, and this small change in discharge current can be detected with great sensitivity by the detector 454. This discharge current reproduces the atomic transition spectra, because the gas discharge itself serves as a resonant photodetector.

Moreover, the reference spectral profile 1117 of the light beam 110' can be determined (1025) by deconvolving the intrinsic transition profile 1111 from the spectral shape of the light beam 110' within the detected convolved transition profile 1113 (1116). The reference spectral profile 1117 therefore is able to remove broadening of the spectral profile of the light beam 110' due to the environment in which the material 148 is held. For example, Doppler broadening due to the broadening of the known energy transition due to the Doppler effect caused by a distribution of velocities of the atoms or the molecules within the material 148 would cause a broadening of the intrinsic transition profile 1111 and the convolved transition profile 1113 and by deconvolving the intrinsic transition profile 1111 from the detected convolved transition profile 1113, the Doppler broadening can be removed from the reference spectral profile 1117.

In some implementations, the deconvolution is performed by computing the Fourier Transform (C) of the convolved transition profile 1113, which is the recorded signal at step 1114, computing the Fourier Transform (I) of the intrinsic transition profile 1111, which is recorded at step 1112, and applying a deconvolution in the Frequency domain to solve for R, which is the Fourier Transform of the reference spectral profile 1117. The reference spectral profile 1117 is the inverse Fourier Transform of R.

The intrinsic transition profile 1111 can be stored within memory 900 for future measurements. Thus, for example, some time can pass between the step of detecting the intrinsic transition profile 1111 (1112) and detecting the convolved transition profile 1113 (1114). And, during this time, the intrinsic transition profile 1111 can be stored within memory 900 and accessed when needed for a future deconvolution (1116).

Figure 12A:
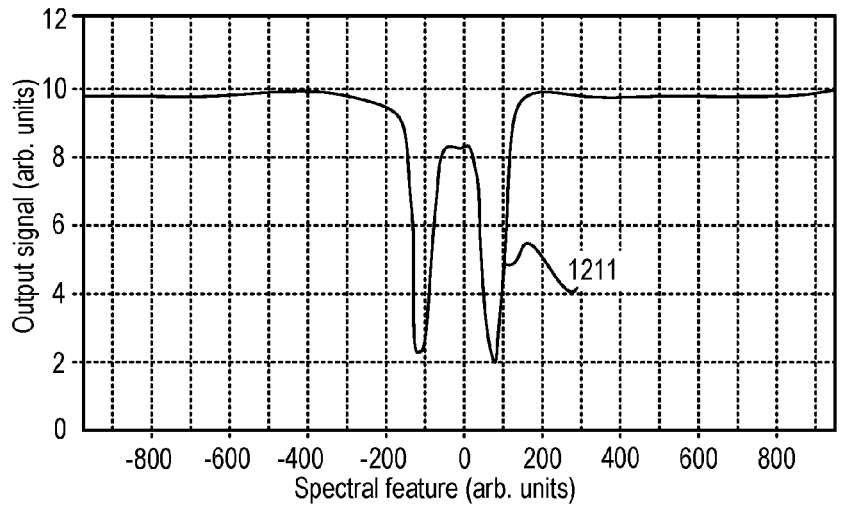
FIG. 12A is a graph of an exemplary intrinsic transition profile detected by the calibration apparatus of FIG. 1.

Referring also to FIG. 12A, an exemplary intrinsic transition profile 1211 that is produced at step 1112 is shown. The intrinsic transition profile 1211 is obtained from interacting the calibration light beam 153 (which is produced from a single frequency all-solid-state laser system in which the gain medium is pumped by a diode laser) with a material that is platinum. FIG. 12A shows the output from the detector 154 (which can be in arbitrary units) as a function of the wavelength of the calibration light beam 153. The output from the detector 154 can be a measure of the current passing through the platinum gas discharge or it can be a measure of the intensity of the calibration light beam 153 after it exits the material 148. For example, if the detector 154 is a photodiode detector that senses the calibration light beam 153, then the profile 1211 can be given as a voltage value directly output from the photodiode detector as a function of the scanned wavelength. The photodiode detector signal is linearly proportional to the intensity of the calibration light beam 153 incident on the photodiode detector. Thus, when the calibration light beam 153 is in resonance with the known absorption transition of the material 148, the intensity of the calibration light beam 153 drops after passing through the material 148 because part of the intensity or photons of the calibration light beam 153 are absorbed by the material 148. The absorbed energy can be released by the material 148 again in a form of fluorescence. In other implementations, the detector 154 is set up to detect the fluorescence from the known absorption transition.

The energy transition of platinum that is probed by the calibration apparatus 145 is an electron energy transition at about 193.4369 nm. In this example, the horizontal axis of the graph has a value of 0 at the center of the electronic transition of the material 148 (thus, 0 corresponds to the energy transition at 193.4369 nm). As the calibration light beam 153 is scanned through this transition, the material 148 absorbs the photons within the calibration light beam 153 and the intensity of the calibration light beam 153 drops. In this example, as shown, there are actually two electron transitions at the wavelength of 193.4369 nm and thus the signal output displays to drops in the signal intensity. The two electron transitions are clearly exhibited by the two drops in the signal from a baseline of about 10 (in arbitrary units) of the output signal to about 2 arbitrary (arb.) units at two distinct locations along the horizontal axis, namely, at about −110 arb. units and about 90 arb. units.

Figure 12B:
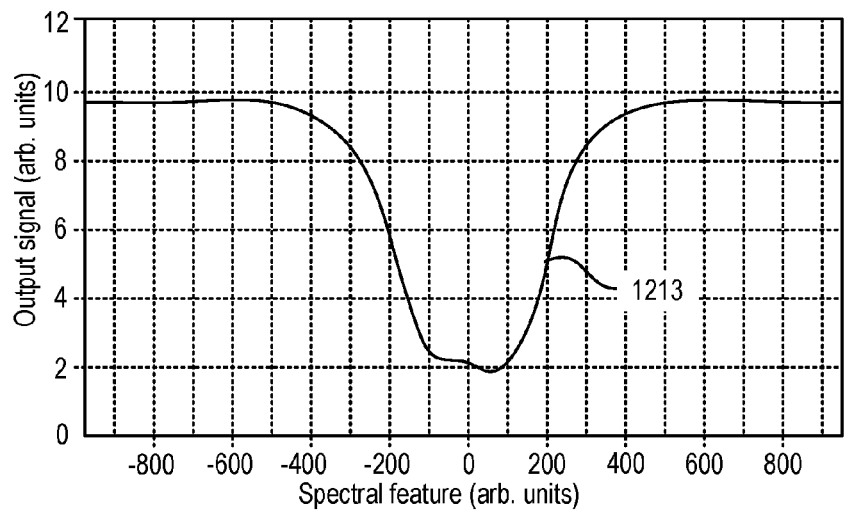
FIG. 12B is a graph of an exemplary convolved transition profile detected by the calibration apparatus of FIG. 1.

Referring to FIG. 12B, an exemplary convolved transition profile 1213 that is produced at step 1114 is shown. This exemplary convolved transition profile 1213 is obtained from interacting the light beam 110' with the platinum material that is used to produce the intrinsic transition profile 1211 shown in FIG. 12A. Because this transition profile is a convolution of the intrinsic transition profile 1211 with the broader spectral shape of the light beam 110', the two energy transitions that are evident in FIG. 12A are not resolved in FIG. 12B.

Figure 12C:
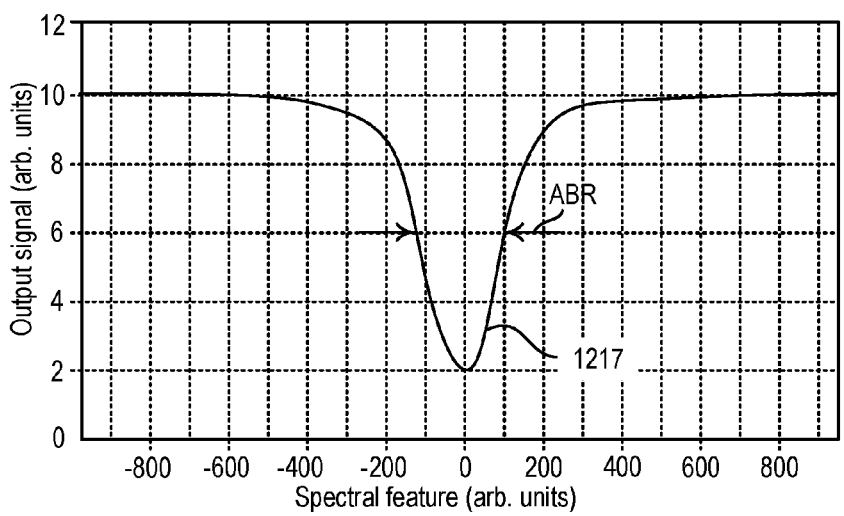
FIG. 12C is a graph of an exemplary reference spectral profile determined by the control system of FIG. 9.

Referring to FIG. 12C, an exemplary reference spectral profile 1217 that is produced at step 1116 is shown. This reference spectral profile 1217 is obtained by deconvolving the intrinsic transition profile 1211 from the spectral shape of the light beam 110' within the convolved transition profile 1213, as discussed above. The absolute bandwidth reference (ABR) can be determined from the reference spectral profile 1217 (as shown in FIG. 12C), and the bandwidth W of the sensed spectral profile can be compared with this value of the ABR at step 1030 (FIG. 10).

Figure 13:
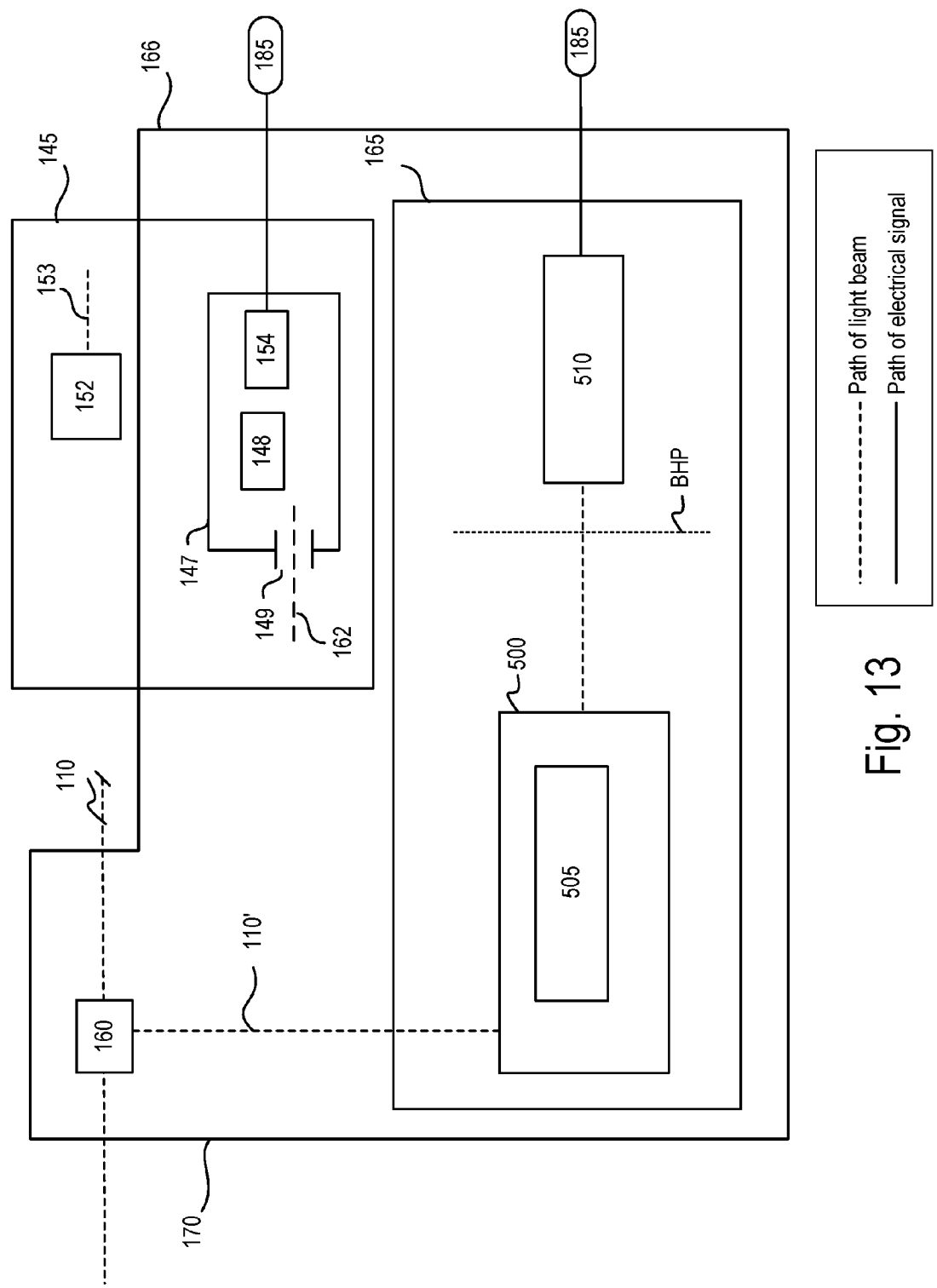
FIG. 13 is a block diagram showing a calibration tool housed within one or more housings associated with the metrology system of the photolithography system of FIG. 1.

Referring to FIG. 13, in some implementations, the calibration tool 147 (which includes an aperture 149 and at least one detector 154 that communicates with the control system 185 as well as the material 148) can be housed within a housing 166 that is associated with the metrology system 170. For example, the housing 166 can also house one or more components of the metrology system 170 such as the spectral detection system 510 or the beam preparation system 500. The housing 166 can house both the spectral detection system 510 and the calibration tool 147, or the housing 166 can house all of the spectral detection system 510, the calibration tool 147, and the beam preparation system 500.

Other implementations are within the scope of the following claims.

What is claimed is:

1. A method comprising:
   detecting an intrinsic transition profile of a known energy transition of a calibration material by detecting a characteristic associated with the interaction between the calibration material and a calibration light beam while the calibration light beam is directed through the calibration material and while the wavelength of the calibration light beam is scanned across the known energy transition;
   detecting a convolved transition profile in which the intrinsic transition profile is altered by a spectral shape of a primary light beam, wherein detecting the convolved transition profile comprises detecting a characteristic associated with the interaction between the calibration material and the primary light beam while the primary light beam is directed through the calibration material and while the wavelength of the primary light beam is scanned across the known energy transition;
   deconvolving the intrinsic transition profile from the spectral shape of the primary light beam within the detected convolved transition profile to determine a reference spectral profile of the primary light beam;
   sensing a spectral profile of the primary light beam, the spectral profile including an optical energy of the primary light beam distributed over different values of a spectral feature;
   comparing the reference spectral profile of the primary light beam with the sensed spectral profile of the primary light beam; and
   adjusting a scale of the different values of the spectral feature at which the spectral profile of the primary light beam is estimated based on the comparison.

2. The method of claim 1, wherein detecting the characteristic associated with the interaction between the calibration material and the calibration light beam comprises detecting an aspect of the calibration material that changes as an amount of absorption of the calibration light beam by the calibration material changes.

3. The method of claim 2, further comprising producing a discharge plasma of the calibration material, wherein detecting the aspect of the calibration material that changes comprises detecting an electrical property of a discharge plasma of the calibration material.

4. The method of claim 1, wherein detecting the characteristic associated with the interaction between the calibration material and the primary light beam comprises detecting an aspect of the calibration material that changes as an amount of absorption of the primary light beam by the calibration material changes.

5. The method of claim 1, further comprising storing the intrinsic transition profile.

6. The method of claim 1, wherein sensing the spectral profile of the primary light beam comprises sensing the optical energy of the primary light beam distributed over different values of the wavelength of the primary light beam.

7. The method of claim 6, wherein comparing the reference spectral profile of the primary light beam with the sensed spectral profile of the primary light beam comprises comparing two or more values of the reference spectral profile with two or more values of the sensed spectral profile.

8. The method of claim 7, wherein:
   comparing two or more values of the reference spectral profile with two or more values of the sensed spectral profile comprises comparing a relative distance between the two or more values of the reference spectral profile of the primary light beam with a relative distance between two or more values of the sensed spectral profile of the primary light beam; and
   adjusting the scale of the different values of the spectral feature at which the spectral profile of the primary light beam is sensed based on the comparison comprises adjusting the scale if the relative distance of the reference spectral profile of the primary light beam is different from the relative distance of the sensed spectral profile of the primary light beam.

9. The method of claim 1, further comprising, after adjusting the scale:
   estimating a spectral profile of the primary light beam;
   estimating a spectral feature of the primary light beam based on the estimated spectral profile;
   determining if the estimated spectral feature is within an acceptable range of spectral features; and
   if the estimated spectral feature is not within an acceptable range of spectral features, then modifying one or more properties of the primary light beam to adjust the spectral feature.

10. The method of claim 1, wherein adjusting the scale of the different values of the spectral feature at which the spectral profile of the primary light beam is sensed based on the comparison comprises adjusting the scale if it is determined during the comparison that the sensed spectral profile of the primary light beam does not match with the reference spectral profile of the primary light beam.

11. The method of claim 1, wherein adjusting the scale of the different values of the spectral feature at which the spectral profile of the primary light beam is estimated comprises adjusting a relative distance between two or more values of wavelength of the primary light beam.

12. The method of claim 1, wherein the known energy transition includes an electron transition, a vibrational transition, or a rotational transition.

13. An apparatus comprising:
   a calibration apparatus comprising:
      a calibration light source that produces a calibration light beam; and
      a calibration material having an optical transition profile with a known energy transition;
   a detector configured to:

detect an intrinsic transition profile of the known energy transition of the calibration material by detecting a characteristic associated with the interaction between the calibration material and the calibration light beam while the calibration light beam is directed through the calibration material and while the wavelength of the calibration light beam is scanned across the known energy transition; and detect a convolved transition profile in which the intrinsic transition profile is altered by a spectral shape of a primary light beam, wherein detecting the convolved transition profile comprises detecting a characteristic associated with the interaction between the calibration material and the primary light beam while the primary light beam is directed through the calibration material and while the wavelength of the primary light beam is scanned across the known energy transition;

a spectral analysis module placed in the path of the primary light beam, the spectral analysis module including a spectral detection system that senses a spectral profile of the primary light beam, the spectral profile including an optical energy of the primary light beam distributed over different values of a spectral feature; and a control system connected to the detector and to the spectral detection system, and configured to:
deconvolve the intrinsic transition profile from the spectral shape of the primary light beam within the detected convolved transition profile to determine a reference spectral profile of the primary light beam;
compare the reference spectral profile of the primary light beam with the sensed spectral profile of the primary light beam; and
adjust a scale of the different values of the spectral feature at which the spectral profile of the primary light beam is estimated based on the comparison.

14. The apparatus of claim 13, wherein:
the detector is configured to detect the characteristic associated with the interaction between the calibration material and the calibration light beam by detecting an aspect associated with an absorption profile of the calibration light beam by the calibration material; and
the detector is configured to detect the characteristic associated with the interaction between the calibration material and the primary light beam by detecting an aspect associated with an absorption profile of the primary light beam by the calibration material.

15. The apparatus of claim 13, wherein:
the calibration material comprises platinum;
the known energy transition is an electron transition at 193.4 nanometers; and
the platinum is in a vapor or a plasma state.

16. The apparatus of claim 13, wherein the spectral analysis module includes an optical frequency separation apparatus that receives the primary light beam and is configured to interact with the primary light beam and to output a plurality of spatial components that correspond to the spectral components of the primary light beam, and the spectral detection system receives the plurality of spatial components.

17. The apparatus of claim 13, wherein the calibration material is housed within a cell, and the calibration apparatus includes a housing in which the detector and the cell are configured, the housing including an aperture that permits the calibration light beam or the primary light beam to pass.

18. The apparatus of claim 13, wherein the known energy transition includes an electron transition, a vibrational transition, or a rotational transition.

19. The apparatus of claim 13, wherein the control system is configured to adjust the scale of the different values of the spectral feature at which the spectral profile of the primary light beam is estimated if it is determined during the comparison that the sensed spectral profile of the primary light beam does not match the reference spectral profile of the primary light beam.

20. The apparatus of claim 13, wherein:
the characteristic associated with the interaction between the calibration material and the calibration light beam that is detected by the detector is an electrical property of a discharge plasma of the calibration material as the calibration material and the calibration light beam interact; and
the characteristic associated with the interaction between the calibration material and the primary light beam that is detected by the detector is an electrical property of a discharge plasma of the calibration material as the calibration material and the primary light beam interact.

21. The apparatus of claim 20, wherein the calibration material is produced as a discharge plasma from an electrode.

22. The apparatus of claim 13, wherein the calibration material is housed within a hermetically-sealed cell, and the cell includes an input window and an output window, the input window and the output window being optically transmissive to the wavelength of the calibration light beam and the wavelength of the primary light beam.

23. The apparatus of claim 13, wherein the calibration light source includes a single frequency laser and the calibration light beam operates in a single resonator mode.

24. The apparatus of claim 13, wherein:
the characteristic associated with the interaction between the calibration material and the calibration light beam that is detected by the detector is an intensity of the calibration light beam that has interacted with the calibration material; and
the characteristic associated with the interaction between the calibration material and the primary light beam that is detected by the detector is an intensity of the primary light beam that has interacted with the calibration material.

25. The apparatus of claim 13, wherein the calibration apparatus includes an enclosure that houses the calibration material and the detector, and the enclosure is within either a housing of the spectral analysis module or a housing of the spectral detection system.

* * * * *